(12) United States Patent
Schulte et al.

(10) Patent No.: US 10,629,303 B2
(45) Date of Patent: Apr. 21, 2020

(54) SYSTEMS AND METHODS FOR DETERMINATION OF PATIENT TRUE STATE FOR PERSONALIZED MEDICINE

(71) Applicant: Apixio, Inc., San Mateo, CA (US)

(72) Inventors: Darren Matthew Schulte, San Francisco, CA (US); John O. Schneider, Los Gatos, CA (US); Vishnuvyas Sethumadhavan, Mountain View, CA (US); Robert Derward Rogers, Pleasanton, CA (US)

(73) Assignee: APIXIO, INC., San Mateo, CA (US)

( * ) Notice: Subject to any disclaimer, the term of this patent is extended or adjusted under 35 U.S.C. 154(b) by 810 days.

(21) Appl. No.: 14/672,208

(22) Filed: Mar. 29, 2015

(65) Prior Publication Data
US 2015/0269337 A1 Sep. 24, 2015

Related U.S. Application Data

(63) Continuation-in-part of application No. 14/538,798, filed on Nov. 11, 2014, now Pat. No. 10,580,520, and
(Continued)

(51) Int. Cl.
*G16H 50/20* (2018.01)
*G06Q 50/24* (2012.01)
(Continued)

(52) U.S. Cl.
CPC .............. *G16H 50/20* (2018.01); *G06F 19/00* (2013.01); *G06Q 50/24* (2013.01); *G16H 50/50* (2018.01); *G16H 10/60* (2018.01); *G16H 40/20* (2018.01)

(58) Field of Classification Search
CPC ........ G16H 50/20; G16H 50/50; G16H 40/20; G16H 10/60; G06F 19/00; G06Q 50/24
See application file for complete search history.

(56) References Cited

U.S. PATENT DOCUMENTS 5,307,262 A * 4/1994 Ertel ..................... G06Q 50/22
705/2
7,321,861 B1 1/2008 Oon
(Continued)

FOREIGN PATENT DOCUMENTS

KR 10-2009-0050881 5/2009

OTHER PUBLICATIONS

USPTO, ISA/US, "Notification of Transmittal of the ISR and the Written Opinion of the International Searching Authority, or the Declaration," in PCT Application No. PCT/US14/66196, dated Apr. 2, 2015, 8 pages.
(Continued)

*Primary Examiner* — Linh Giang Le
(74) *Attorney, Agent, or Firm* — Kang S. Lim

(57) ABSTRACT

Systems and methods for personalizing medicine utilizing the true state of the patient are provided. A number of medical records for a patient are subjected to predictive modeling for various conditions (known as patient 'true state'). The patient personal information, previous care, and true state may be provided into a state machine in order to determine the resources needed for the patient. The medical resources may be any of laboratory services, diagnostics, therapies and medications. Using the true state information, and number of activities may be performed for the patient based upon the patient's needs. These activities include scheduling lab or diagnostic procedures in advance of an appointment, filling in documentation gaps, identifying items that require additional documentation using the true state, and tracking follow-up. It may also be beneficial to validate the true state.

20 Claims, 20 Drawing Sheets

Related U.S. Application Data a continuation-in-part of application No. 13/656,652, filed on Oct. 19, 2012, now Pat. No. 8,898,798, application No. 14/672,208, which is a continuation-in-part of application No. 14/498,594, filed on Sep. 26, 2014, now Pat. No. 10,600,504.

(60) Provisional application No. 62/059,139, filed on Oct. 2, 2014, provisional application No. 61/682,217, filed on Aug. 11, 2012, provisional application No. 61/883,967, filed on Sep. 27, 2013.

(51) Int. Cl.
*G16H 50/50* (2018.01)
*G06F 19/00* (2018.01)
*G16H 10/60* (2018.01)
*G16H 40/20* (2018.01)

(56) References Cited

U.S. PATENT DOCUMENTS

| | | | |
|---|---|---|---|
| 2002/0188182 A1* | 12/2002 | Haines | A61B 5/0002 600/300 |
| 2005/0043986 A1 | 2/2005 | McConnell | |
| 2005/0138017 A1 | 6/2005 | Keen et al. | |
| 2006/0036619 A1 | 2/2006 | Fuerst et al. | |
| 2006/0047669 A1 | 3/2006 | Durrence et al. | |
| 2006/0129435 A1 | 6/2006 | Smitherman et al. | |
| 2007/0016450 A1 | 1/2007 | Bhora et al. | |
| 2007/0055545 A1 | 3/2007 | Maughan et al. | |
| 2007/0219829 A1 | 9/2007 | Kay | |
| 2008/0091633 A1 | 4/2008 | Rappaport et al. | |
| 2008/0120296 A1 | 5/2008 | Kariathungal et al. | |
| 2008/0263048 A1 | 10/2008 | Wise | |
| 2008/0270340 A1 | 10/2008 | Abrams et al. | |
| 2009/0024615 A1 | 1/2009 | Pedro et al. | |
| 2009/0070103 A1 | 3/2009 | Beggelman et al. | |
| 2009/0112882 A1 | 4/2009 | Maresh et al. | |
| 2009/0136102 A1 | 5/2009 | Kimpe et al. | |
| 2009/0271221 A1 | 10/2009 | Aridi et al. | |
| 2010/0117799 A1 | 5/2010 | Dormer et al. | |
| 2010/0131299 A1 | 5/2010 | Hasan et al. | |
| 2010/0169123 A1 | 7/2010 | Maus et al. | |
| 2010/0179827 A1 | 7/2010 | McCallie, Jr. et al. | |
| 2010/0185496 A1 | 7/2010 | Hahn et al. | |
| 2010/0324936 A1 | 12/2010 | Vishnubhatla et al. | |
| 2011/0078145 A1 | 3/2011 | Chung et al. | |
| 2012/0066017 A1 | 3/2012 | Siegel | |
| 2012/0284056 A1 | 11/2012 | Hofstetter | |
| 2013/0159023 A1 | 6/2013 | Srinivas et al. | |
| 2013/0297536 A1 | 11/2013 | Almosni et al. | |
| 2013/0332194 A1* | 12/2013 | D'Auria | G16H 10/60 705/3 |
| 2014/0278832 A1 | 9/2014 | Glavina | |
| 2015/0066539 A1* | 3/2015 | Sheffer | G06Q 50/22 705/3 |

OTHER PUBLICATIONS

Korean Intellectual Property Office, ISA, "International Search Report and Written Opinion" in PCT Application No. PCT/US2012/053182, dated Mar. 18, 2013, 12 pages.

* cited by examiner

| | 1 | 2 | 3 | 4 | 5 | 6 | 7 | 8 | 9 | 10 | 11 | 12 |
|---|---|---|---|---|---|---|---|---|---|---|---|---|
| | Name | DOC SB | BP DATE | BPs | BPd | LDL Date | LDL | A1c DATE | A1c | DIABETIC | SMOKER | DATE ASKED IF SMOKES |
| | Patient A | NO | 2/1/2011 | 127 | 70 | 1/30/2010 | 93 | | | NO | NO | 11/30/2010 |
| | Patient B | YES | 2/15/2011 | 110 | 55 | 2/15/2011 | 145 | 9/25/2010 | 11.3 | YES | YES | 2/15/2011 |
| | Patient C | NO | 4/7/2010 | 158 | 87 | 4/11/2010 | 81 | 4/11/2010 | 6.7 | YES | NO | 3/15/2008 |
| | Patient D | YES | 1/20/2011 | 148 | 96 | 12/14/2010 | 170 | 12/14/2010 | 8.9 | YES | YES | 12/12/2009 |
| | Patient E | NO | 10/26/2010 | 129 | 72 | 12/10/2010 | 54 | 12/10/2010 | 9.8 | YES | YES | 3/30/2010 |
| | Patient F | NO | 8/21/2010 | 125 | 88 | 4/20/2010 | 125 | | | NO | NO | |
| | Patient G | YES | 6/24/2010 | 149 | 85 | 4/16/2009 | 102 | | | NO | NO | 12/2/2008 |
| | Patient H | NO | 3/5/2011 | 147 | 90 | 3/5/2011 | 81 | 3/5/2011 | 12.1 | YES | NO | 3/5/2011 |
| | Patient I | NO | 1/29/2010 | 120 | 64 | 2/3/2010 | 65 | | | NO | NO | 12/22/2004 |
| | Patient J | YES | 1/5/2011 | 117 | 81 | 1/5/2011 | 112 | 1/5/2011 | 5.9 | YES | YES | 7/5/2010 |
| | Patient K | YES | 7/24/2008 | 153 | 85 | 7/14/2008 | 157 | | | NO | | |

1800

SYSTEMS AND METHODS FOR DETERMINATION OF PATIENT TRUE STATE FOR PERSONALIZED MEDICINE

CROSS REFERENCE TO RELATED APPLICATIONS

This non-provisional application claims the benefit of and is a continuation-in-part of co-pending U.S. patent application Ser. No. 14/538,798 filed on Nov. 11, 2014 entitled "Systems and Methods for Medical Information Data Warehouse Management."

This non-provisional application additionally claims the benefit of and is a continuation-in-part of co-pending U.S. provisional patent application No. 62/059,139, filed on Oct. 2, 2014, entitled "Systems and Methods for Medical Information Management."

Also, this application claims the benefit of and is a continuation-in-part of co-pending U.S. non-provisional patent application Ser. No. 13/656,652, filed on Oct. 19, 2012, now U.S. Pat. No. 8,898,798, which in turn is a continuation-in-part of co-pending U.S. non-provisional patent application Ser. No. 13/223,228, filed on Aug. 31, 2011, which claims the benefit of U.S. provisional patent application 61/379,228, filed on Sep. 1, 2010, expired. Application Ser. No. 13/656,652 also claims the benefit of U.S. provisional patent application No. 61/682,217, filed on Aug. 11, 2012, expired.

Additionally, this application is a continuation-in-part of co-pending U.S. non-provisional patent application Ser. No. 14/498,594 filed on Sep. 26, 2014, which in turn claims the benefit of U.S. provisional application No. 61/883,967, filed on Sep. 27, 2013, expired.

Further, this application is related to co-pending U.S. non-provisional application Ser. No. 14/672,206, being filed concurrently herewith, entitled "Systems and Methods for Determination of Patient True State for Risk Management" (Our Ref: APX-1501).

All above-referenced applications listed above are hereby fully incorporated in their entirety by this reference.

BACKGROUND

The present invention relates generally to systems and methods for determination of patient true state using automated first pass review of patient medical records. Knowledge of the true state of a patient (determination of patient condition) enables management of coding risks, as well as enhanced patient management and record retention abilities. Some embodiments of the present systems and methods enable more accurate and rapid capture of MediCare eligible conditions, thereby ensuring providers are more fairly compensated, and ensure that medical records more accurately reflect a patient's condition.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One common problem with the analysis of medical records is that identification of clinically pertinent conditions is often not properly identified, and further, even when identified, the evidence in the patient records to support such a finding is not always properly referenced. Moreover, the process for verifying a condition is often time consuming and labor intensive. This results in a few issues, including: MediCare compensation difficulties, missing of important health conditions and/or misdiagnosis, and lastly the clouding of medical analytics with incomplete or incorrect data.

The first issue, compensation by MediCare, results in providers being underpaid for work performed. This may cause many providers to shy away from MediCare patients, increases cost on other patients, and generally leads to inefficiencies in the administration of government backed medical coverage. Additionally, miss-coding of MediCare claim opens providers to potential audit risk.

The second issue, improper or incomplete diagnosis, can be extremely detrimental to the patient. Often early treatment of a condition results in a far better prognosis for the patient. In the extreme, delays of treatment may reduce the patient's life expectancy. As such, there is a very compelling reason to ensure the medical information of a patient is properly documented, with a high degree of accuracy.

In addition to these direct health impacts to the patient, improper or incomplete diagnosis of the patient can lead to unnecessary tests or follow-ups, which can be financially taxing as well as a drain on the resources of the medical community. Thus there are also tangible financial implications to proper diagnosis with supporting evidence.

Lastly, incorrect or missing data may result in the skewing of analytics performed using the medical records. The medical community is entering into an age of big data analysis. These analyses of large data sets of aggregated medical records generated best practices and means for refining a medical practice. It also enables early detection of health trends and patient behavior. Using these results, medical professionals have the opportunity to greatly increase the efficiency of the administration of medical services. This translates directly into improved patient care at reduced costs. However, such analysis relies upon datasets that are accurate. When the input data is flawed, or incomplete, the analysis suffers.

It is therefore apparent that an urgent need exists for improved means for recordation and analysis of medical records. In particular, the clinical state of patients may be determined using a computerized system, which then enables a host of subsequent activities, including: 1) enhanced personalized medicine, 2) coding audit risk management, 3) more complete and accurate record keeping for providers, and 4) MediCare reimbursement optimization via the identification of coding opportunities.

SUMMARY

To achieve the foregoing and in accordance with the present invention, systems and methods for personalizing medical care are provided. In some embodiments, the true state of the patient is utilized in order to tailor the personalized care to a given patient.

Initially a number of medical records for a patient are received. These records are subjected to predictive modeling for various conditions (known as patient 'true state'). The true state is utilized to identify medical resources that may be useful for the patient. Additionally, a confidence interval may be determined for the true state finding.

In some embodiments, the patient personal information, previous care, and true state may be provided into a state machine in order to determine the resources needed for the patient. The medical resources may be any of laboratory services, diagnostics, therapies and medications.

Using the true state information, and number of activities may be performed for the patient based upon the patient's needs. These activities include scheduling lab or diagnostic procedures in advance of an appointment, filling in documentation gaps, identifying items that require additional documentation using the true state, and tracking follow-up.

In some embodiments it may also be beneficial to validate the true state. The validation process updates the predictive model and updates the confidence level for the inferred true state. Optimized routing on the evidence used for validation may be employed. This routing ensures that evidence that has the greatest impact on the true state inference is presented first.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 14-17 provide example screenshots of annotated medical records, in accordance with an embodiment;

FIG. 18 provides an example screenshot of a data warehouse management spreadsheet, in accordance with an embodiment.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary Note that, for the purposes of this disclosure, the term "first pass" refers to the automated computer process by which medical records for one or more patients may be parsed and analyzed for patient conditions such as diseases, other information regarding their state such as lab values, medications that they are on, biometric values etc. . . . The first pass process may also be referred as patient "classification".

These "patient conditions" may be referred to as the patient's "true state", "status" or "finding". These terms may be utilized interchangeably throughout the present disclosure. Additionally, the patient's condition may be an actual disease state, pre-disease state, or other medical classification.

Also note that the following disclosure includes a series of subsections to aid the clarity of the following disclosure. Such subsections are not intended to artificially limit the scope of the disclosure. As such, any disclosure in a particular subsection may be equally applicable to another section as is applicable.

I. Medical Systems

Figure 1:
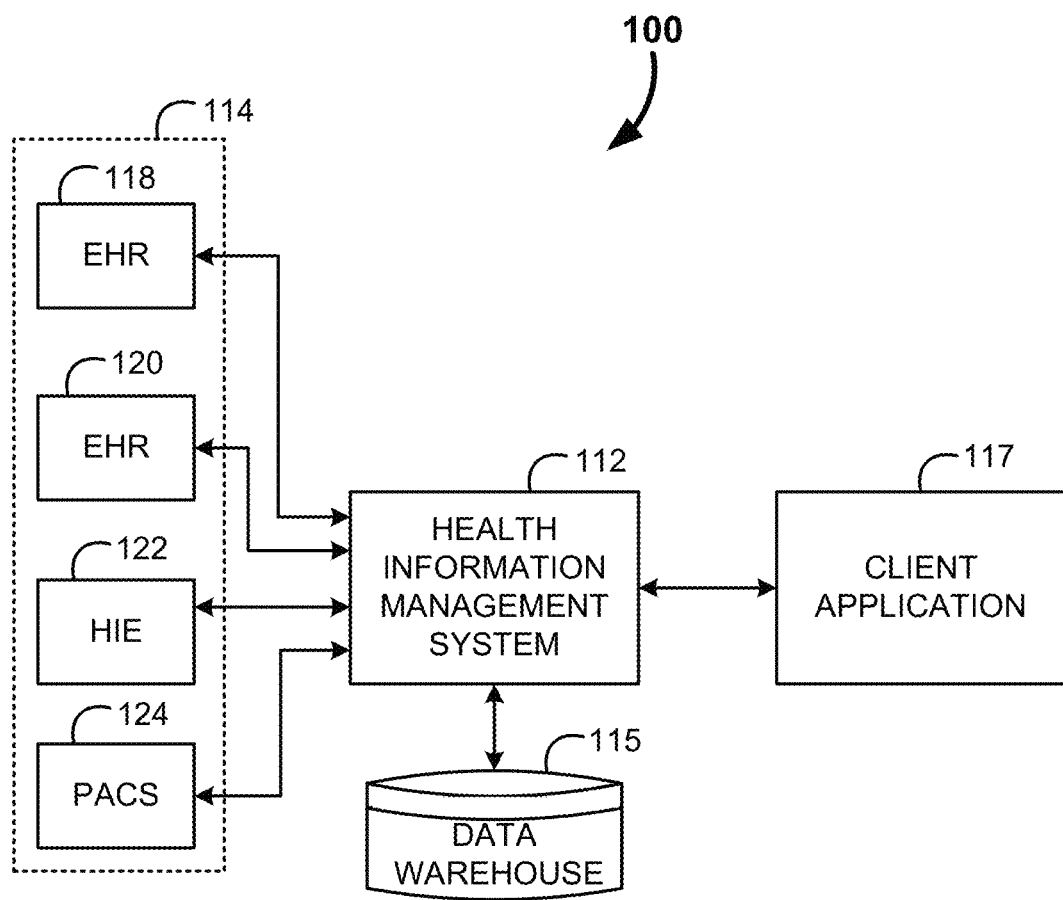
FIG. 1 shows a medical system, in accordance with an embodiment.

Referring now to FIG. 1, a medical system 100 is shown, in accordance with some embodiments. The system 100 is shown to include medical information sources 114, a health information management system 112, and medical information consumers/client applications (also referred to herein as "output" or "medical output") 117. The medical sources 114 are shown to include one or more electronic health record (EHR) 118, EHR 120, health information exchange (HIE) 122, and a picture archiving and communication system (PACS) 124, among other known sources of medical information.

"Medical information", as used herein, may refer to any health-related information, including but not limited to patient medical records, patient entered information, care team entered information, healthcare device generated information, and billing information.

The sources 114 generally provides various medical information to the health information management system 112. For example, the EHRs 118 and 120 each may provide information such as medical records and billing, the HIE 122 may provide information such as medical records, and the PACS 124 may provide information such as diagnostic imaging and reports.

The medical information consumers/client applications 117, which may be made of a host of entities or individuals, such as patients, clinics, medical institutions, health organization, and any other medical-related party, use information that is provided by the health information management system 112. For example, user-customized processed medical information is provided by the health information management system 112 to a number of client applications 117. In this case, the health information management system 112 generates user-customized processed medical information to a plurality of users, with at least a portion of the user-customize processed medical information being provided to each of the users based on the relevancy of the portion being provided of each user's specific function or role and each user's associated security privileges.

In some embodiments, the health information management system may merely be a repository of health records and information. In alternate embodiments, the health information management system 112 may have sophisticated capabilities which enable it to index, map, and consolidate medical information, received from the sources 114, and also potentially enabling the tagging of this information, and reconciliation of the tagged information. In some methods and embodiments, information that is extracted from images is tagged to enhance recall of search queries. Indexing, at least in part, processes document and converts them into formats that allows for quick searching across a large collection of documents.

In pertinent embodiments, the health information management system 112 may include data warehouse management and condition classification functionalities. In some embodiments, the information in the health information management system 112 is encrypted and secure to ensure privacy of sensitive medical information.

It is understood that the sources 114 of FIG. 1 includes merely some examples of the sources that communicate with the health information management system 112 and that other sources, known to those in the field, are contemplated. Similarly, the output 117 may be used by those or entities not discussed herein but that are contemplated and within the scope and spirit of the invention.

Figure 2:
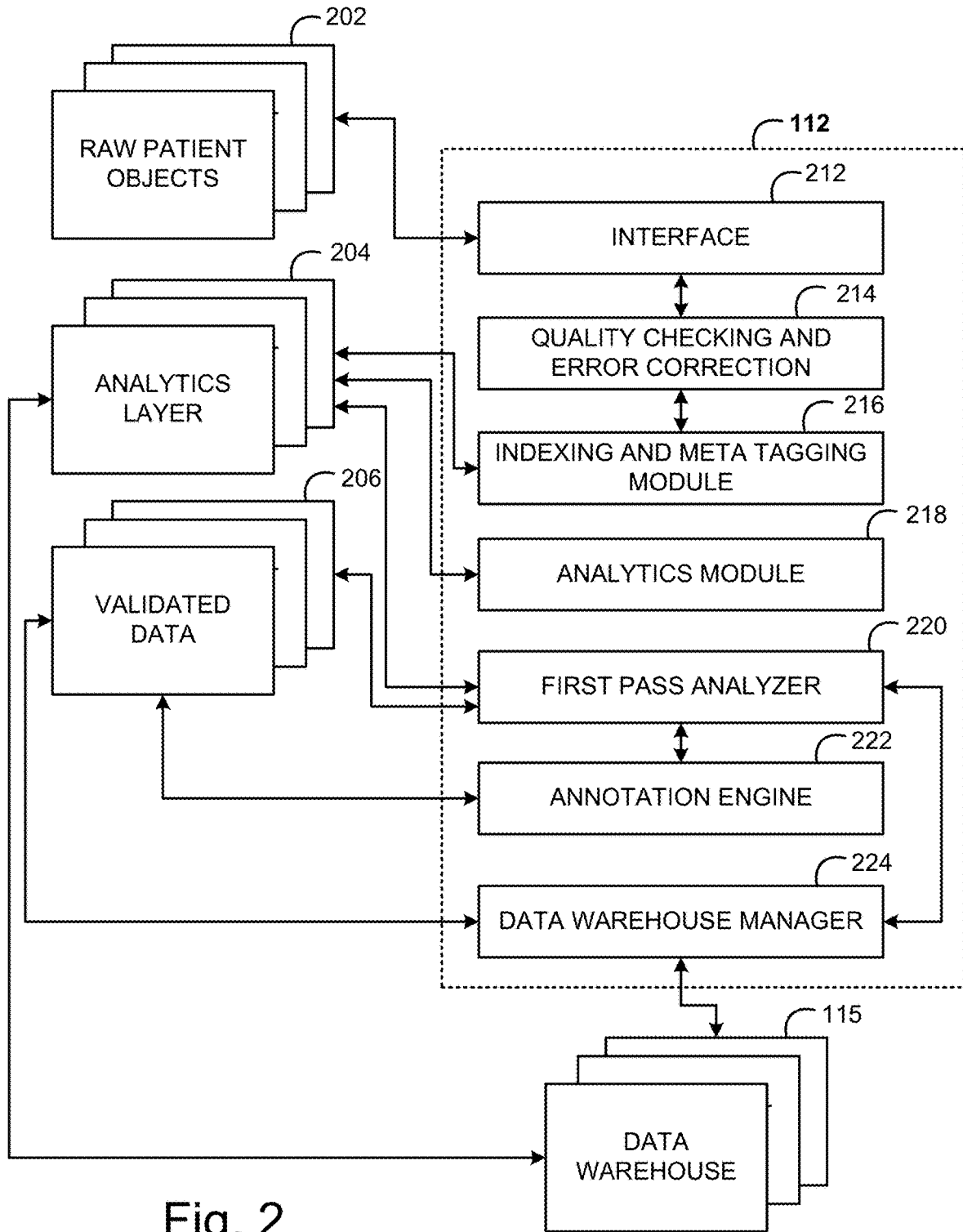
FIG. 2 shows further details of the system within a data architecture, including a first pass analyzer, annotation engine and data warehouse manager, in accordance with an embodiment.

Turning to FIG. 2, a more detailed illustration for the health information management system 112 is provided. In this example diagram, the health information management system 112 is interacting with multiple levels of data storage. The storage level begins with raw patient objects 202 which are received from the plurality of sources 114.

The health information management system 112 includes an interface 212 which can collect these objects. These objects 202 may be collected in various forms, such as but not limited to text, html, CCD, CCR, HL7 and any other type or formatted information. The interface 212 then provides to the information to a quality checking and error corrector 214, in some embodiments.

The quality checking and error corrector 214 may simply delete duplicate errors and redundant patient medical records, such as, multiple records for the same individual appearing as though the records are for different individuals, or multiple data elements that are recorded similarly but slightly differently in the different sources. The quality checking and error corrector 214 may also perform other basic and known error correction processes. Alternatively, more advanced quality checking and error corrector 214 systems may check the quality of medical information provided by various sources 114 by the patients, structured data, and unstructured data, in a Wiki-like mannered setting whereby the users can help maintain and improve the quality of information displayed.

In some embodiments, an indexing and Meta tagging module 216 may utilize a processor to processing the data, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others. The processed data may then be provided to the second level of the data storage architecture, the analytics layer 204. In some embodiments, the analytics layer 204 may be transient.

An analytics 218 module may take information from the analytics layer 204 and perform certain tasks on the information, which may include query, search, presentation, and quality checking. The output of the analytics 218 may be stored within the analytics layer of the data architecture, or may be stored in a logically separate layer of the data structure, known as the application optimized data.

In some embodiments the analytics module 218 may employ natural language processing (NLP) techniques to parse and syntactically analyze the machine readable records in order to identify medical terms, and concepts. The first pass analyzer 220 may then employ predictive models to the records to make probabilistic determinations of likely conditions for a patient associated with the medical records. Part of the determination includes assigning a confidence value to the finding based upon historical accuracy of the predictive model and the evidence used to generate the finding. In some embodiments, the first pass analyzer 220 may further be able to parse through multiple medical records, and perform chronological analysis to determine a finding. For example, if a patient is seen for a physical and shows abnormally high glucose levels, and is then scheduled for a follow-up a month later that confirms a diabetic condition, the system may be able to extrapolate that the diabetic condition likely existed as early as the initial physical exam.

It should be noted that many means for NLP are known in the art, and likewise predictive modeling is likewise a rich field. It is intended that any such known art may be employed to effectuate the above disclosed analysis of medical records. This includes adaptive predictive modeling that is updated as additional data becomes available, rule based NLP, etc.

Findings by the first pass analyzer 220 may be subject to validation by a user to improve the predictive modeling algorithms, as well as hone accuracy estimates for the first pass analyzer 220. The results of such validations, as well as the validated findings, may be stored within a validated data layer 206.

After the medical records have been analyzed for findings, the output may be utilized by an annotation engine 222 to confirm the findings and provide customized annotations to the records. It is currently required that findings used for MediCare compensation be reviewed by a human operator prior to submission. This validation is often time consuming and requires significant coder time and effort to identify the evidence of the finding and properly validate. The annotation engine 220 enables rapid highlighting of the relevant evidence and seamless presentation to the coder for validation and annotation of the evidence. Moreover, the first pass analyzer 220, in some embodiments, may be enabled to pre-populate the records with annotations that may be readily viewed, approved, declined or edited by an annotator for even faster review.

This process has been shown to increase the speed of validation by a coder by twenty to forty times traditional validation processes. In addition, it has been found that the accuracy of findings is increased by these validation processes. Results of the validation and associated annotations may be incorporated into a final data wrapper stored in a data warehouse 115. The financial implications of this capability are enormous, enabling more efficient healthcare administration.

The validated finding, annotation (if provided), and associated documents are stored within a data warehouse 115. A data warehouse manager 224 may access this data warehouse 115 in order to enable NLP probabilistic transformation of the source documents into a standardized and structured data set. The structured data set includes links from the extracted values to the source documents, thereby enabling a user to rapidly reference back to the source for a given finding. When referencing the source documentation the user may update the information, including the addition of annotations, when required, and ensures that data is provided to the user in the most efficient means possible. In alternate embodiments, the data warehouse manager 224 is able to provide non-validated, annotated records for coder review, and subsequent validation.

Below, each of the first pass analyzer 220, annotation engine 222, and data warehouse manager 224 will be provided in greater detail. These detailed descriptions of these system components are provided by way of example, and it is understood that other logical and/or physical configurations are considered within the scope of this disclosure.

1) First Pass Analyzer

Figure 3:
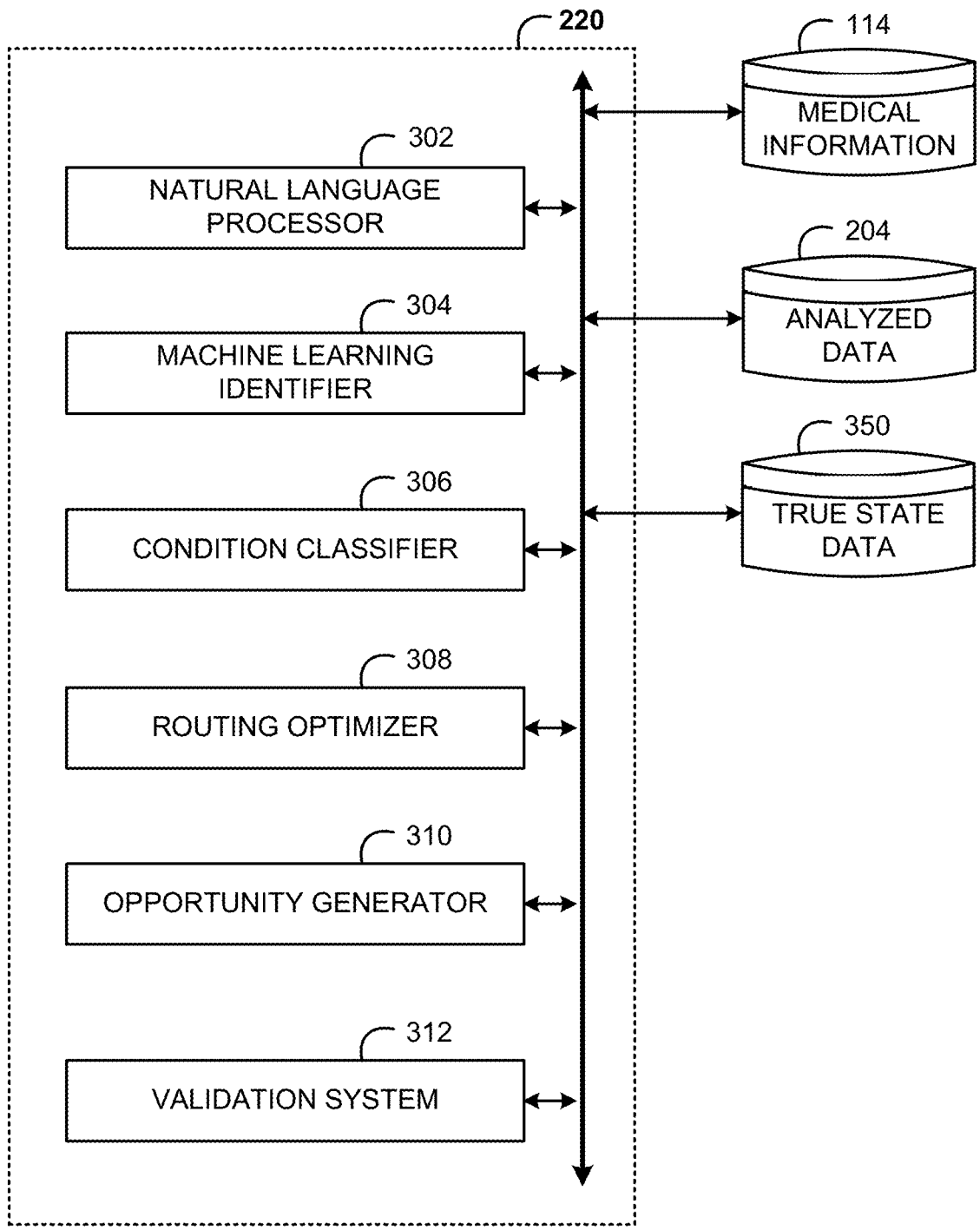
FIG. 3 shows an exemplary embodiment of the first pass analyzer, in accordance with an embodiment.

FIG. 3 provides a more detailed block diagram of an embodiment of the first pass analyzer 220. The first pass analyzer is integral to the ability to determine patient true state, and therefore enables the audit risk reduction and personalized medicine that the presently disclosed system provides. In this example, medical information 114 is provided in either raw form, or as an analyzed form 204, as previously disclosed. The data analyzed by the first pass analyzer 220, at a minimum, typically include past claims, problem lists, procedures, lab data, medication lists, symptom data, and the like. The data includes textual data, images that have been converted into machine readable text, and raw images (such as a chart or x-ray image).

A natural language processor 302, in conjunction with a machine learning identifier 304, identifies terms and concepts within the data. In some embodiments, the language nodes identified are cross referenced against a Wiki-like database which relationally clusters various terms with a medical concept. For example, a glucose rating within a specific range may be associated with "diabetes" as a medical concept. Likewise, the drug Colesevelan Hcl (a bile acid sequestering compound) may also be associated with diabetes as well as cholesterol management. Thus, this drug may be associated with a number of medical concepts.

The medical concept data gained via natural language processing and machine learning may be provided to the condition classifier 306, which utilizes probabilistic models to determine what the patient's true state 350 is, and the estimated accuracy of the true state inference. For example, the patient is seen as having slightly elevated glucose levels in a lab (120 mg/dl). This evidence in and of itself is insufficient to make any determinations of diabetic state. However, the patient is likewise seen to have an earlier glucose level of 160 mg/dl before taking Colesevelan Hcl. Any one piece of this information, taken independently, would be a poor indicator of a diabetic state for the patient. After all, the glucose levels are not particularly high, and the medication is often associated with cholesterol management. However, when taken in aggregate, including the shift in glucose lab numbers over time after the medication is applied, strengthens a finding of diabetes for the true state of this patient. For example, in one embodiment, any of the above evidence would only indicate a 20-30 percent chance of diabetes as the true state. However, when modeled in aggregate, the probability of diabetes as the true state rises to above 90%.

Through validation of the findings, as will be discussed in more detail below, the probabilistic modeling accuracy may be estimated, and modeling accuracy may be continually improved. The routing optimizer 308 may be utilized to determine which evidence should be presented for validation. This system calculates which evidence has the largest impact on determination of the true state of the patient. This impact may be a measure of money per time, or audit risk per time.

After determining which evidence is to be prioritized for validation, the evidence may be routed to a user for validation via the validation system 312. Validation includes presenting the evidence to a qualified user and requesting the user to either provide a finding for the evidence from scratch, or provide feedback for the finding generated by the system. This may be as simple as providing a 'yes' or 'no' selection for the finding where the evidence is highlighted for the user's convenience.

The feedback collected from the validation system 312 may be incorporated into the models to refine the accuracy of the condition classifier 306, and also provide accuracy measures of the true states already determined.

The opportunity generator 310 identifies areas where there is some evidence for a true state, but not enough to produce a finding with a high degree of certainty, and/or evidence that indicates a particular true state for the patient, but is insufficient for documentation for generating a claim. This stems from the fact that the presently disclosed sophisticated system is able to perform probabilistic determinations that is able to draw out true state information from disparate evidentiary sources. Under this type of multivariable analysis, conclusions may be generated from evidence that is considered relatively weak when viewed individually. In contrast, in order to submit a code under MediCare, the evidence required must be fairly robust. Indeed, the evidence must be contained in a single document and meet particular requirements.

In order for a medical record to be submitted to Medicare for reimbursement for a condition, regulations require that the medical record be the result of a face-to-face encounter between the physician and the patient, signed, and by a correct specialist. Contextual clues within the document may be employed to ensure that the face-to-face requirement has been met. This may include explicit statements, such as "patient arrived at the clinic at 2:00", or may include inferences of the patient being present. For example, the medical record could indicate that the patient had blood drawn as part of the diagnosis, which requires the patient being present. Additionally, document metadata may be employed to make this determination.

For example, a document may not admissible for specific reimbursement purposes (eg: Medicare HCC) unless it has been signed by the physician. Image recognition algorithms may be employed to ensure a signature is present. Advanced embodiments, may even perform signature matching between the document and a repository of signatures to ensure the document is authentic. Additionally, document metadata may be employed to make this determination.

Certain conditions can only be validly diagnosed by specific physicians. For example, a podiatrist may be able to diagnose conditions that an oncologist is not allowed to, and vice versa. The system compares the physician specialty to the condition and compares the match to a table of allowable diagnoses for the specialist.

Often a document may be missing one or more of the above requirements, and may further lack MEAT (Monitor, Evaluate, Assess and Treat) documentation sufficient to qualify for reimbursement from MediCare. However, if the true state is determined with a fair degree of confidence, this opens up a reimbursement opportunity for the system.

2) Annotation Engine

Figure 4:
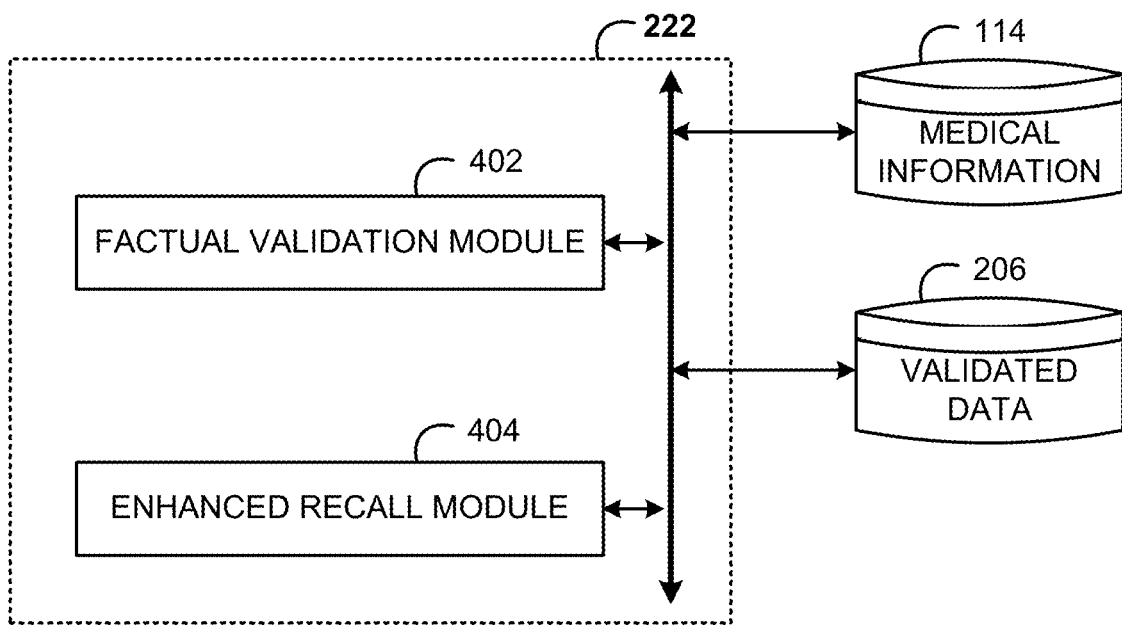
FIG. 4 shows an exemplary embodiment of the annotation engine, in accordance with an embodiment.

FIG. 4 provides a more detailed block diagram of an embodiment of the annotation engine 222. In this example, medical information 114 is provided in either raw form, or as an analyzed form, as previously disclosed. In order to perform annotation, a set of findings is typically required. These findings may be provided from the disclosed first pass analyzer 220, as previously discussed, or the findings may have been identified via more traditional means, such as manual analysis of the medical records by coder.

The annotation engine 222 includes two logically distinct subcomponents, a factual validation module 402 and an enhanced recall module 404. The subsystems may operate in tandem to generate validated and annotated data 206 as a final output. The validated data may include the validated finding, any associated annotations, and associated evidence/documents. This validation may operate in tandem with the validation system 312 of the first pass analyzer 220. In some embodiments, these may be logically indistinct systems.

The factual validation module 402 takes a finding and highlights the evidence for the coder. The highlighting may include literally highlighting of the evidence in a source document, or may include other known techniques to readily display pertinent evidence. When more than one source of evidence is available for the specific finding, the system may present the evidence that is most compelling. In the case where a predictive model has been utilized to make the finding, the evidence associated with the highest confidence rating may be displayed. When the finding has been generated by human coders, analytics regarding coder accuracy may be employed to present the "best" coder's evidence. Alternate evidence may likewise be made available to the user performing the validation as a hyperlink or embedded attachment.

The coder performing the validation may be queried whether the finding is correct via a simple yes/no selection option, or may include a more elaborate toggle option for more granular validation.

The enhanced recall module 404 operates in a reverse order by presenting the coder with a finding and a source document, and requesting the coder to validate by highlighting or otherwise flagging the evidence relevant to the finding. This method of validation may be performed in conjunction with, or as an alternate to the specific finding validation process described previously. Recall enhancing mode is used when a model is being developed or in order to validate a known model to identify when the model needs enhancement. This is an iterative process. Factual validation mode is used to refine an existing model by further classifying accuracy of output. This information can be used in the final presentation of a specific result and in an iterative process to improve the accuracy of the model, taking into account the validation data from multiple coders (annotators).

Annotations supplied during factual validation or enhanced recall may be accepted in a free-form customized format. These annotations, and their associations to a particular piece of evidence in a source document, are stored. The annotations may be queried, and the association may be utilized to inform the importance of a particular piece of evidence.

As previously mentioned, predictive models may be employed to determine what evidence is highlighted for the coder before asking for a diagnosis. Likewise predictive models may be employed to determine which source documentation may be presented when a highlight request is made. One unique feature of this system is that the model used, or weights within the model, may be driven by the context of the annotation activity and/or the user engaging the system.

For example, if an annotation is being performed for a MediCare level submission, the predictive model employed will require a higher threshold of confidence, located in a single medical document. This may result in relatively few medical records being identified for annotation compared to a program for identifying patients for follow-up activity related to potential diabetes risk. In such a context, the evidence may have a lower threshold, and may be collected from multiple documents associated with the patient.

3) Data Warehouse Manager

Figure 5:
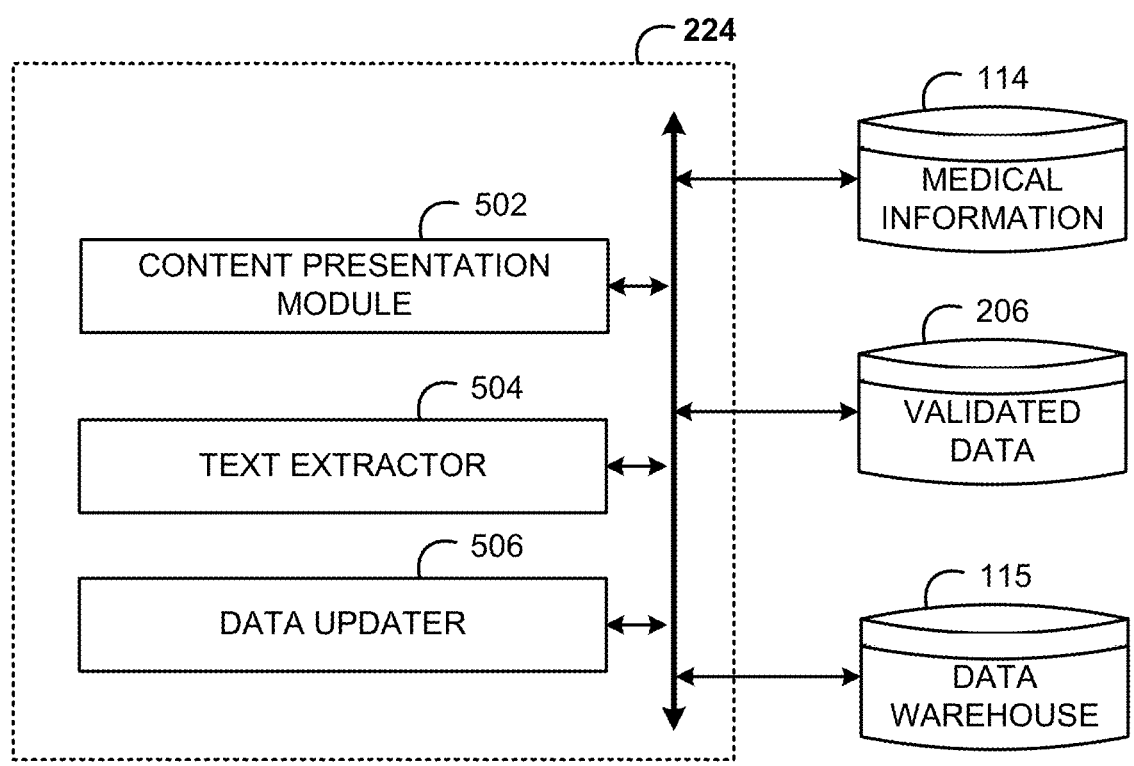
FIG. 5 shows an exemplary embodiment of the data warehouse manager, in accordance with an embodiment.

FIG. 5 provides more detail of the data warehouse manager 224. This system includes a content presentation module 502, a text extractor 504 and a data updater 506 logically coupled together. The content presentation module 502 is enabled to take data from the data warehouse 115 and present it to the user in a tabular (or other condensed form). The content presentation module 502 presents the results of text processing algorithms (for example, machine learning, natural language processing, text search, etc) which perform a probabilistic transformation of the source documentation into a more readily machine readable format (structured format). An example of a structured format that is commonly employed would be a spreadsheet or a relational database table.

A text extractor 504 enhances values from text extraction with a link that enables the user to reference the source documentation for the extracted values with a single click. For example, when the data warehouse 115 information is placed into a tabular structured format, the findings in the table may include links that, when clicked upon, directly provide the source documentation to the user. The source documentation may be presented with evidence highlighted, and annotations labeled, in order to facilitate very rapid review of the finding. The highlighting, as previously discussed, may be literal highlighting, or otherwise identify the pertinent evidence within the source documentation.

As previously mentioned, text highlighted may be contextually driven based upon user looking at the document, or other contextual considerations. As with annotations, when multiple evidence sources for the finding are available, the most accurate evidence is presented first, with an option to view additional evidence.

The user may opt to update the data within the source documentation, such as highlighting new or different information, or adding an annotation. If the user inputs data, the data updater 506 stores these newly updated records within the data warehouse 115.

II. Methods

Now that the systems for the health management system have been disclosed in detail, attention will be directed toward the processes of medical record annotation and validation. These processes are provided in conjunction with exemplary flowcharts. These flowcharts are merely examples of specific embodiments of some processes employed to perform the annotation, coder marketplace management, and data warehouse presentation.

As such, the following flowcharts, and associated text, are intended to be merely illustrations of embodiments, and not limiting the scope of the present invention to any specific embodiment.

1) MediCare Risk Management

Figure 6A:
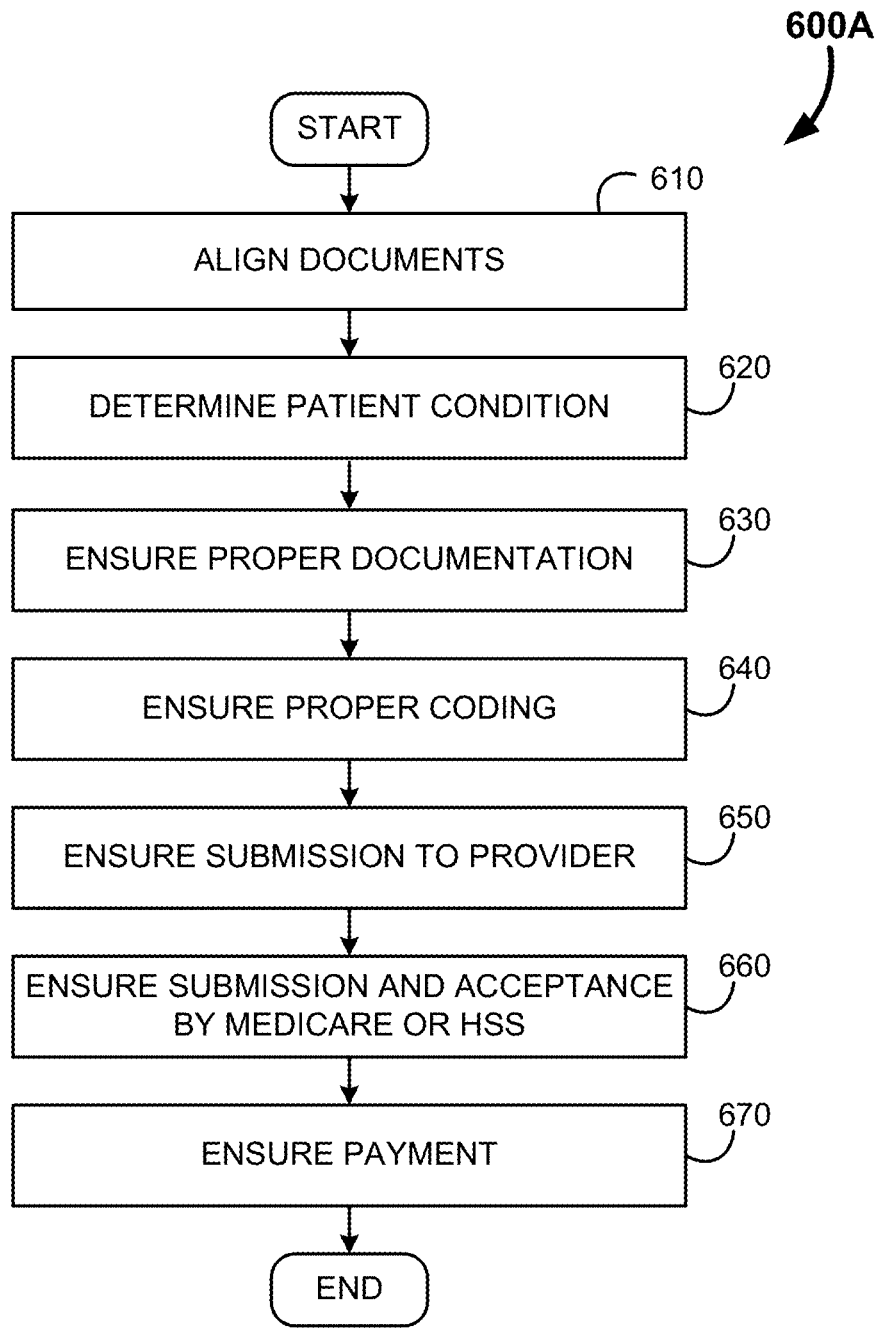
FIG. 6A shows an example flow chart for the process of mitigating coding risk utilizing first pass determination of a patient's true state, in accordance with an embodiment.

FIG. 6A provides a high level overview of one example processes for medical claims risk management and optimization, provided generally at 600A. In this example process, the documents are aligned (at 610). Document alignment includes linking related documents, removal of duplicates, and general documentation cleanup.

Next the patient true state is determined (at 620). This process will be disclosed in greater detail below, and is a major component of the presently disclosure. After the true state has been determined, the system ensures that the documentation provides a proper evidentiary basis for the true state (at 630). Often it is possible that a true state may be determined, but the evidence behind it is insufficient for MediCare reimbursement (as previously discussed). A report of problematic codings is presented here, which reduces audit risks significantly. The problem codings may be corrected, where appropriate. Other times, documentation is missing, which results in a finding being categorized as a problem coding ("red zone"). In such a case, the required documentation may be located and incorporated into the evidentiary record, thereby reducing risks associated with an audit.

As will be described in greater detail below, findings may also be categorized into an intermediate risk level ("yellow zone") which can result in one or more opportunities being generated that can help to increase reimbursement claims, or suggest corrective measures to bolster the evidence behind weakly supported findings.

Next, the proper coding is checked (at 640) to ensure that the codes claimed match the true state (are corresponding documentation). The submission is then tracked as it is submitted to the provider (at 650), and subsequently submitted and accepted by MediCare of HSS (at 660). Lastly the payment is tracked (at 670) to ensure the entire system is closed through completion of the reimbursement.

2) Personalized Medicine and Record Retention

Figure 6B:
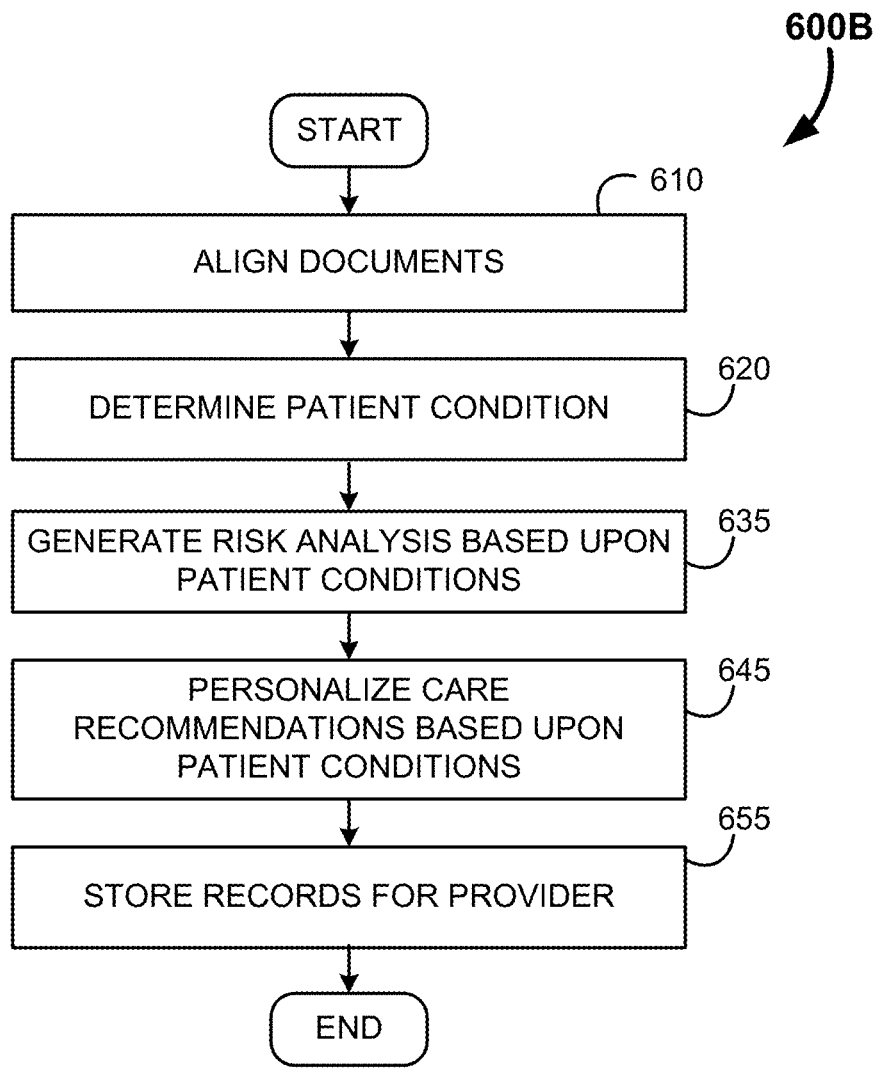
FIG. 6B shows an example flow chart for the process of providing personalized care and record storage, utilizing first pass determination of a patient's true state, in accordance with an embodiment.

FIG. 6B provides a high level overview of one example processes for improving personalized medicine and provider record keeping, provided generally at 600B. This example process may be performed in conjunction or separately from the MediCare risk management process described above. In this example process, the documents are also aligned (at 610), and the patient's true state is determined (at 620). However, at this point, the process diverges from the risk management process discussed above.

Providers have interest in patient record keeping and personalization of their care for a multitude of reasons. First off, more effective care and records enable the patients to have better outcomes. This improves their experiences and quality of living. Secondly, these improvements to records and patient care typically result in significant savings to the provider, which results in lower costs to the patients, and improved profits to the provider.

Catering toward provider needs, the true state data for the patients may be employed to generate risk analysis for a patient cohort (at 635). By understanding the condition of the patients, and understanding the costs associated with these conditions, the financial risk over the next month, year, or longer, may be amortized for the provider.

Next, personalized care recommendations may be generated based upon the patient's true state (at 645). Given the patients care history, personal information and condition, the system may compare possible therapeutic options and determine the most impactful or efficient care options moving forward. Personalized care may include any of: scheduling a patient for an appointment; scheduling labs or diagnostic work in advance of an appointment; highlighting key items that require additional inquiry or documentation for the physician; filling in documentation gaps; tracking follow-up activities; setting up tailored questionnaires for patients; and wellness tracking, or tracking of patient behavior/health maintenance activity. The true state of the patient may even be employed to identify pre-disease states that can be monitored and utilized to head off full disease states.

One example of personalized care is if a patient's true state is determined as being spinal stenosis based upon pain descriptions and a physical exam, and no care has been provided besides a pain medication, the system may recommend a conservative care program. For example, the system could suggest physical therapy and an anti-inflammatory prescription for a set period of time. If there symptoms do not resolve under such conservative care, the system may recommend MRI imaging to provide more information regarding the extent of the senosis, as well as location of the constriction. Once the MRI has been completed, more aggressive options may be undertaken, including cortisone injections and ultimately spinal surgery, if warranted.

For a given starting state, condition, and care already received, the recommendations may be determined utilizing a state machine. For example, assume the above patient were elderly and already taking a steroidal anti-inflammatory (such as meloxicam) for arthritis. In such a circumstance, a cortisone shot may be out of the question due to concerns over excessive steroidal intake. Likewise, due to the patient's age, surgery may be rejected as a therapeutic option. In this case, the recommendations may be directed toward strengthening the spine and pain management rather than rectification of the underlying problem. Thus, a costly MRI may also be avoided as no longer being a required diagnostic tool.

The recommendation and all generated medical records, as well as the patient's true state, may all be retained in a records database (at 655) for the provider. This record keeping may be performed in conjunction with the data warehouse management described in greater detail below.

Records on true states have a number of benefits above and beyond typical electronic health record systems. These true state repositories may be employed to track physician performance within a patient population, for example. Likewise, plans may utilize the true state information of a patient cohort to estimate actuarial risks for pricing determinations. True state information may be utilized to prepare any number of reports, including document coverage for specific specialties, disease areas, provider groups, care sources, specific providers, etc. This allows profiling of providers, groups, organizations all based upon conditions, disease types (chronic vs. acute), or other desired variable.

3) First Pass determination of True State

As noted above, the processes for personalized medicine, and MediCare risk management, all depend upon the process of first pass determination of the patient's true state. Traditionally, this true state must be determined via a physician, and acted upon effectively. The present system allows determination of true state from any number of medical records, even if collected from disparate providers. Further, even if the patient's condition has been already recognized by a physician, the true state determination via first pass of the medical records enables the capture of lost reimbursement opportunities, and as a comprehensive recordkeeping system.

Figure 7:
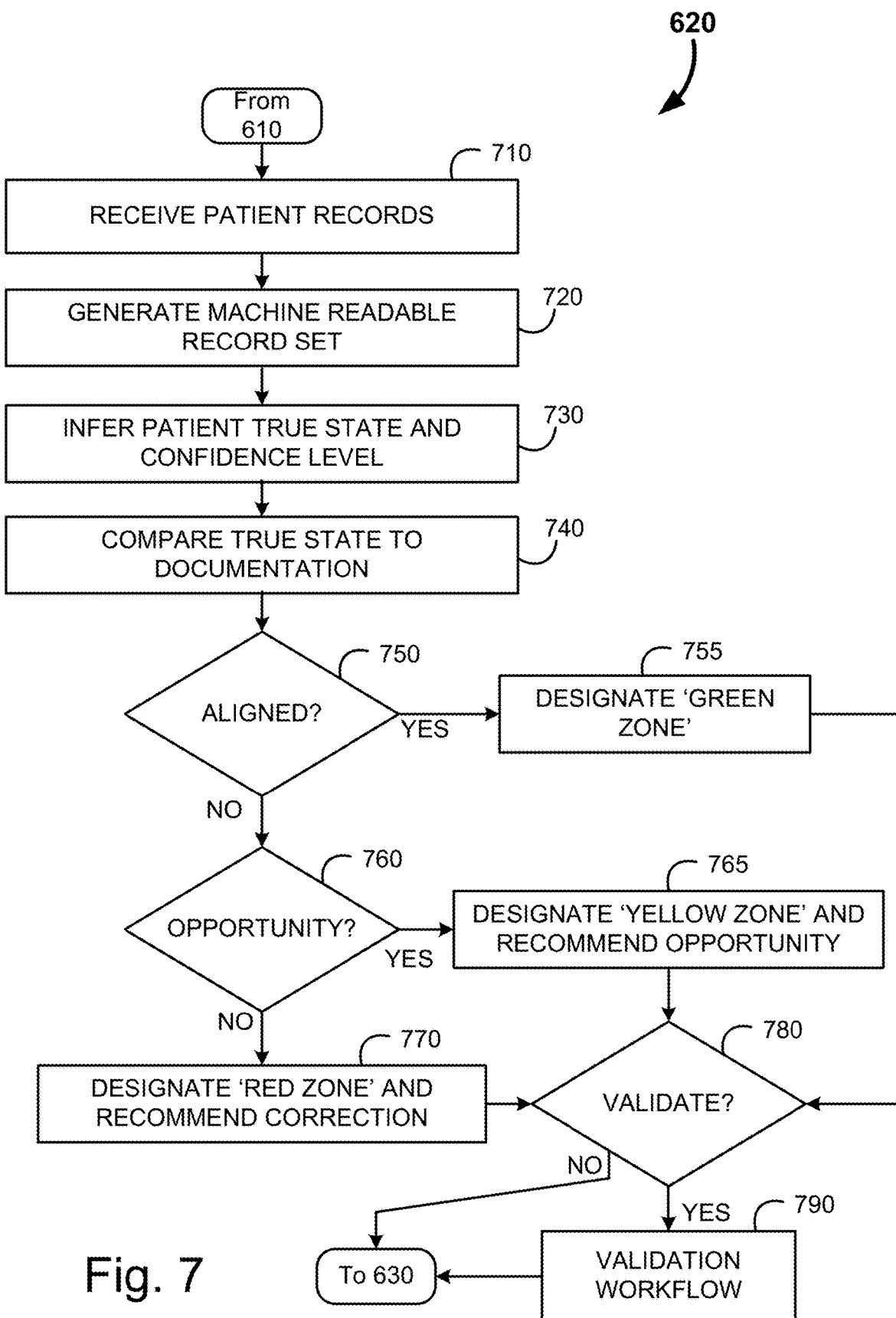
FIGS. 7-11 show example flow charts for the process of first pass determination of a patient's true state, in accordance with an embodiment.

FIG. 7 provides a high level overview of one example processes for true state determination, provided generally at 620. This process begins after the documents have been aligned. The medical records belonging to a single patient are received (at 710) from any of the many sources of medical records previously discussed. The medical records are converted into a machine readable record set (at 720).

The conversion of the data into a machine readable data set may employ known natural language processing techniques, rules based systems, predictive modeling, or any combination thereof. In some embodiments, rule based systems can learn through history, ontology, user-input, the type of user, and a host of other factors, similarities between various information. The system then models the data conceptually by mapping data based on rules for disease/diagnosis relationships, medications, etc. Timing rules may likewise be applied to see how data has changed over time.

Figure 8:
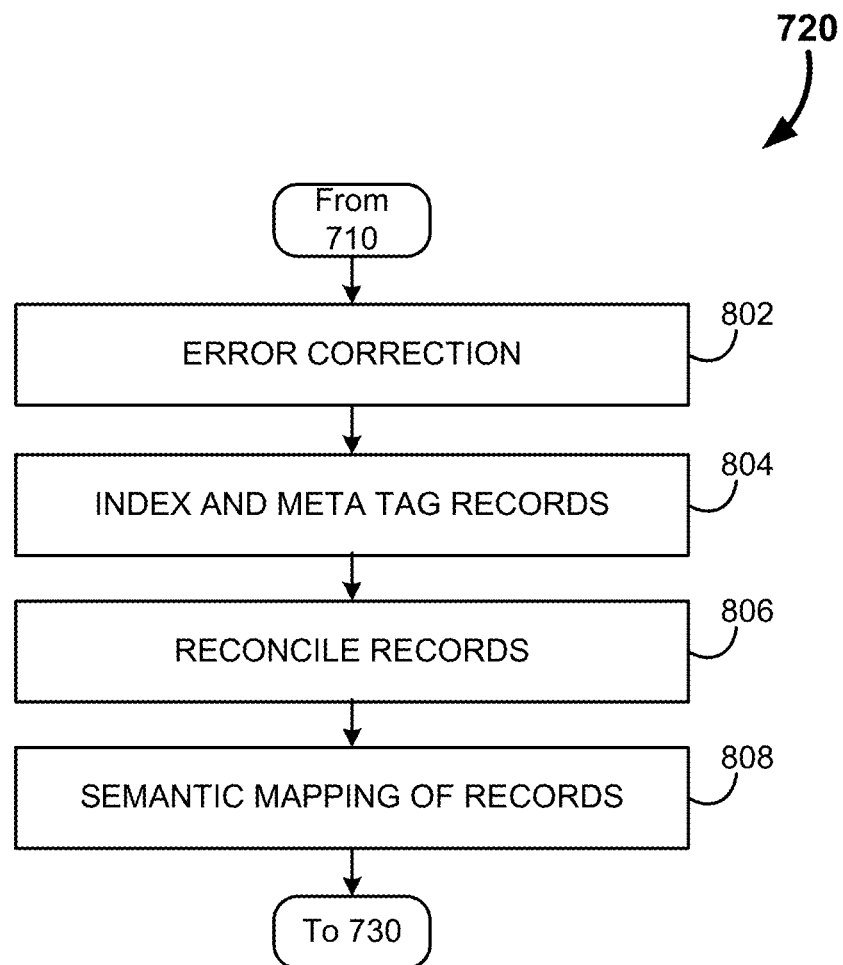

Turning to FIG. 8, a more detailed process flow for the step of converting the medical records into machine readable format is disclosed. Initially an error correction step (at 802) removes duplicate records, incomplete records, and nonsensical records. The corrected records may then be provided for indexing and meta tagging (at 804). Indexing takes processed documents and converts them into formats that make it easy to quickly search across a large collection of documents. Semantic meta-tagging embeds information into the medical information that is relevant thereto and that can be later used to search for certain information for the purpose of reconciliation (at 806) and search, among many others. Next, the records undergo semantic mapping (at 808) as discussed above.

Returning to FIG. 7, the machine readable records are then subjected to predictive modeling to infer the patient's true state and a confidence level for the inference (at 730). The inferred true state may then be compared to the documentation and submitted codes (at 740) to facilitate categorization of codings into risk appropriate groupings. For example, if the documentation and true state are in a high degree of alignment (at 750) then the risk of an incorrect reimbursement request from MediCare is minimal. Such a finding may be designated as being in the 'green zone' (at 755), or any other such designation that indicates that the documentation and factual state are closely aligned. "Green zone" indicates that these findings are well supported via evidence, and are reflective of the patient's true state. These findings are likely to be very low risk if audited by MediCare.

In contrast, when there are some incongruities between the true state and the documentation, it indicates that there is an "opportunity" that may be realized (at 765). As these findings have a greater risk during auditing, these findings are set as belonging in a "yellow zone" (at 765), or other intermediate designation. Additionally, an activity is suggested to capitalize upon the opportunity. This recommendation has the aim of reducing auditing risk, and/or improving patient care.

For example, assume the patient's true state is determined, and there is no code submitted for the true state (despite sufficient evidence). The system may recommend that the code is submitted, and may even present the evidence for the code support. Likewise, assume in another example that the true state is determined, and the code for the condition has been submitted, however the documentation is not sufficient to support the coding if audited. In such a circumstance, the system may recommend that the documentation be readdressed in order to lower audit risk. This may include simple changes to the document, or may necessitate a follow-up with the patient to collect any missing documentation.

In yet another example, a true state may have been determined, but with a relatively low confidence level. The system may thus recommend that the patient be brought back in for a follow-up in order to confirm the true state and generate the documentation required for a MediCare reimbursement.

In this manner, it can be seen that the identification and action upon opportunities leads to collection of previously wasted reimbursements, identification of previously undiagnosed conditions, and protection against costly audits.

However, if during the comparison of the true state and documentation there is no alignment or opportunity identified, then the finding is designated as being in the 'red zone' (at 770), or other least favorable categorization. This circumstance occurs when there is a coding in the system, and no evidentiary support that backs up the finding (i.e., total misalignment of the code and true state). Codes that are located in this "red zone" are susceptible to audit at best, and indicate an error was likely made during the coding process. A correction is recommended for findings in the red zone. Often this includes determining whether there is missing documentation (a common source of codes that are unsubstantiated), or the code was inputted in error.

Regardless of classification in the green, yellow or red zone, the next step in the process is to determine whether a validation is desired for the first pass classification (at 780). As previously mentioned, validation may be performed on an optimized basis in some embodiments. In these cases, the evidence most impactful in determining the true state may be given priority for validation over less impactful documentation.

Figure 9:
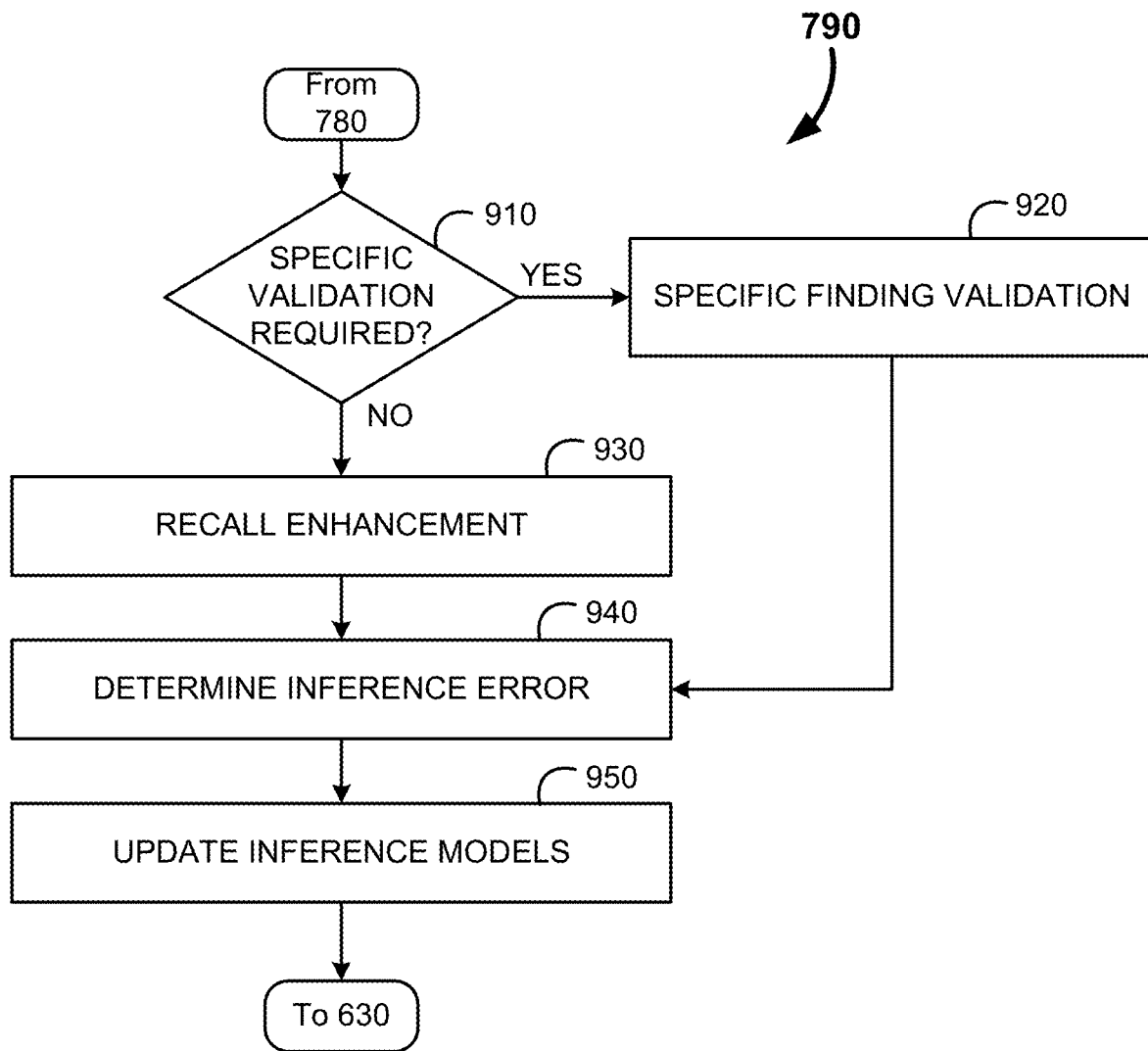
Figure 10:
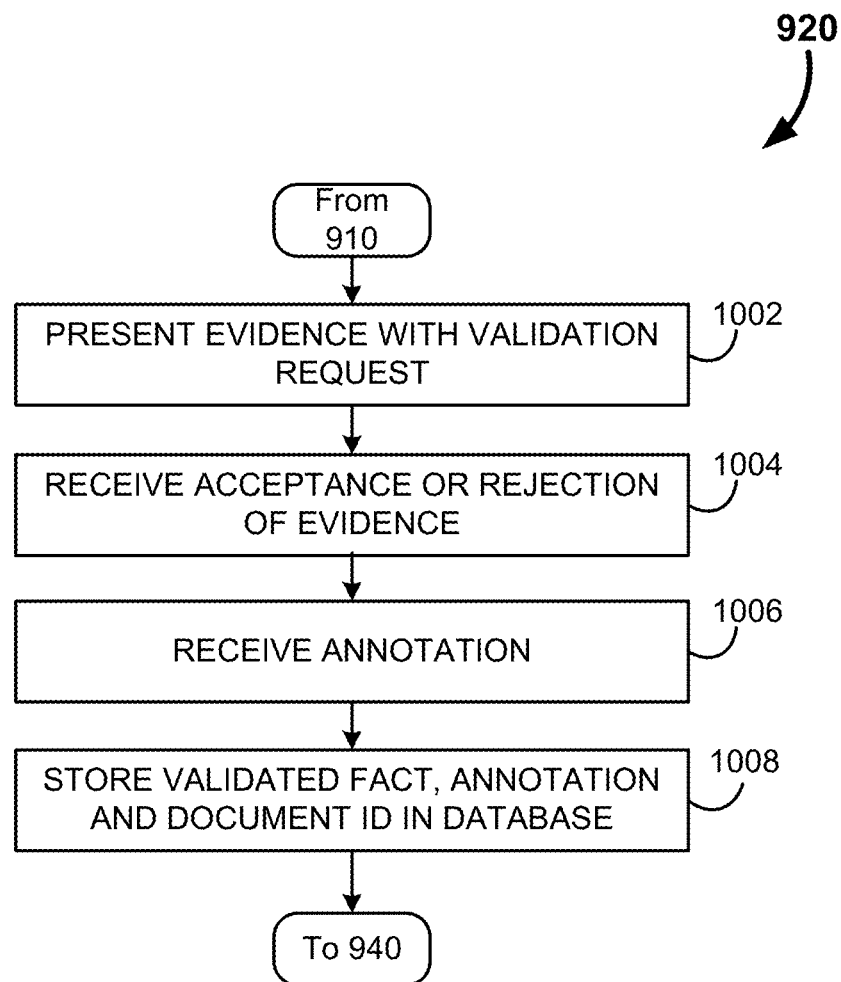
Figure 11:
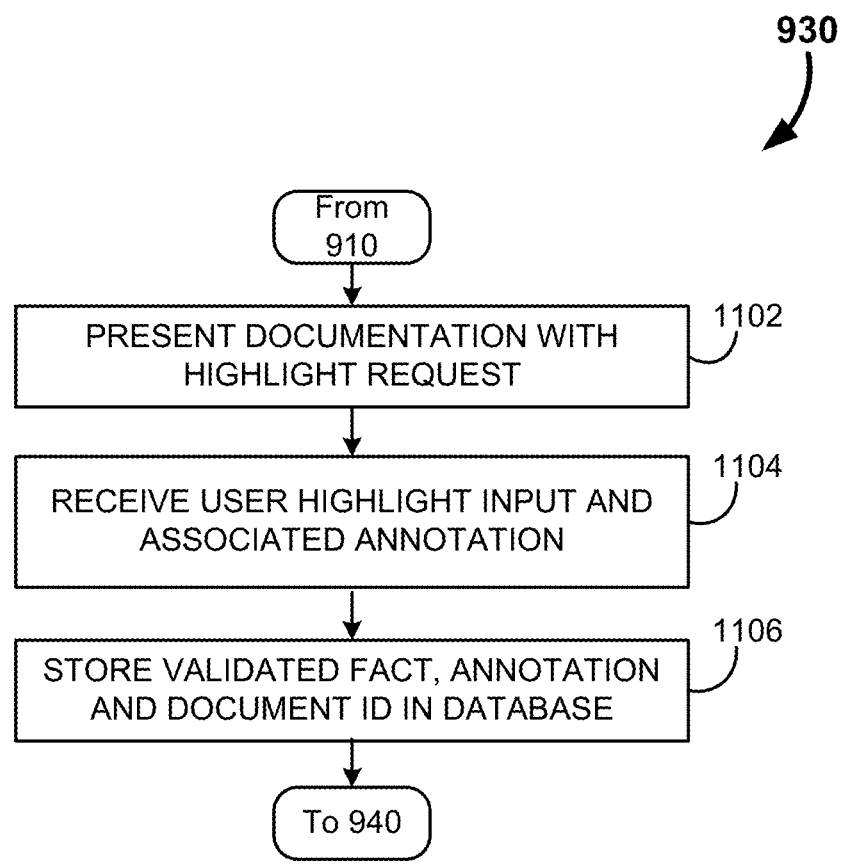

If validation is desired, the validation workflow is pursued, which is provided in greater detail at FIG. 9, shown generally at 790. A query is made whether specific validation of the classification is desired (at 910). If so, the specific finding validation process is performed (at 920). If not, then recall enhancement may be alternately performed (at 930). FIGS. 10 and 11 provide the processes for specific finding validation, and recall enhancement, respectively.

For specific finding validation, at FIG. 10, the evidence is presented to the coder with a validation request (at 1002). This evidence typically includes directly providing the source documentation with the specific evidence highlighted, or otherwise identified, so that the coder is immediately directed to the pertinent information. When multiple sources of evidence are present for a finding, the most accurate may be provided to the coder, with a link or other reference to the additional evidence.

The coder is then able to confirm or reject the finding that is provided (at 1004). The coder is also able to input any annotations at this stage (at 1006). Annotations are customizable free form comments that are associated with a piece of evidence. The annotations are capable of being queried, and the association between the annotation, and highlighted evidence can be leveraged for analytics. Lastly, the validated fact is stored in the data warehouse, along with any annotations, annotation associations, and document ID (at 1008).

In FIG. 11, the process for recall enhancement is provided. In this example process, the source document is provided to the coder with a highlight request (at 1102). In many ways this is opposite the specific finding validation procedure detailed above; instead of requesting a validation of a finding based upon provided evidence, here the finding is provided, and the coder is asked to locate the evidence in the source document.

The user then highlights the relevant evidence that supports the finding, and may also input associated annotations with the highlighted evidence (at 1104). The validated fact is stored in the data warehouse, along with any annotations, annotation associations, and document ID (at 1106).

Returning to FIG. 9, after the specific finding validation and/or recall enhancement validation is performed, the error made in the true state inference is calculated (at 940) relying upon the validation feedback. Likewise, the inference models utilized to perform classifications is updated utilizing the validation feedback (at 950).

After validation, the process of condition classification is complete. The true state information, with corresponding confidence estimates, are then available for subsequent downstream processing, such as used for audit risk management and/or personalized medicine and record keeping, as previously discussed. In some embodiments, the record keeping features enabled by knowing a patients true state may be further enhanced via comprehensive data warehouse management.

4) Data Warehouse Presentation and Management

Figure 12:
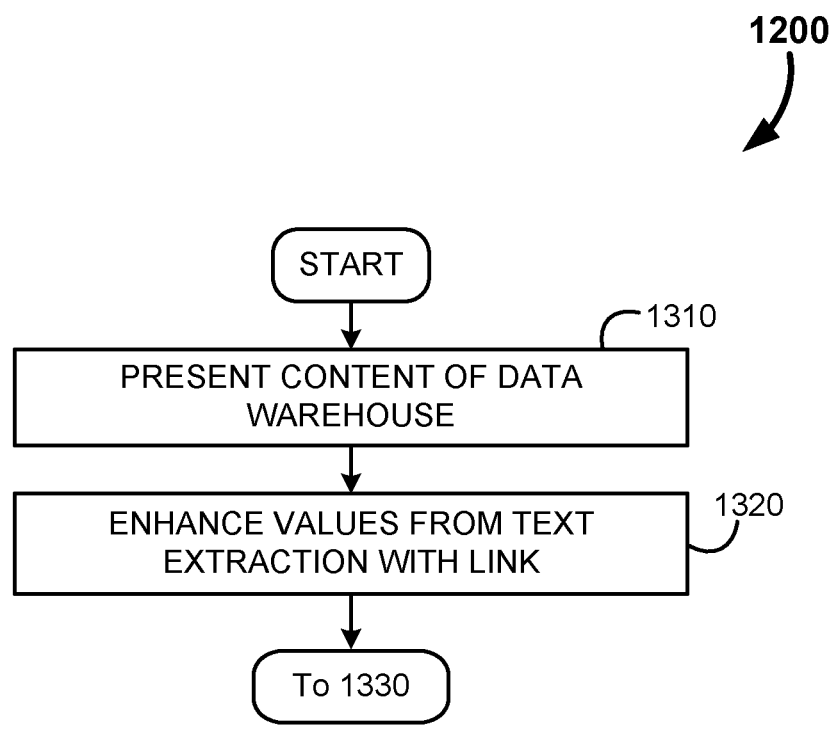
FIGS. 12 and 13 show an example flowchart for the process of managing a data warehouse, in accordance with an embodiment.
Figure 13:
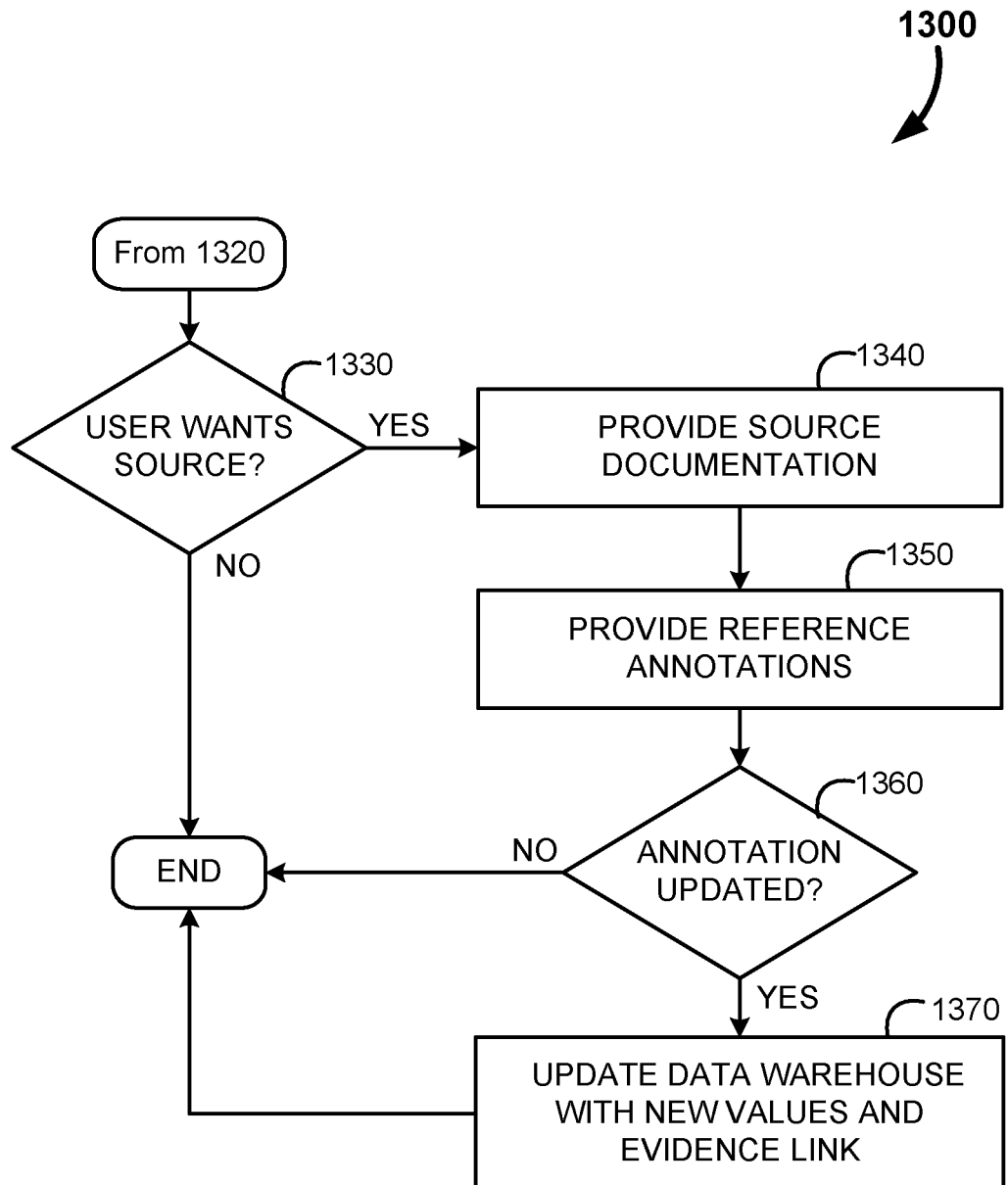

FIGS. 12 and 13 provide the exemplary process of the management of the data warehouse, and particularly how the findings in the source documents may be compiled and presented to the user in a structured format, shown generally at 1200 and 1300.

This process begins by presenting the content of the data warehouse to the user (at 1310). As previously touched upon, this presentation may include earlier classifications and validations of the source documents in order to generate structured data. In some embodiments, natural language processing and predictive models are leveraged to perform probabilistic transformations of the unstructured source documents (and the evidence they contain) into a structured dataset. In some embodiments, this structured dataset may be a tabular summary of the patients, basic chart information, whether they suffer from aliments that are designated, and the inferred true state for the patient. In some cases, the structured data set is configurable by the user. Additionally, the dataset may further be contextually driven such that the data presented matches the intended end use.

For example, in one instance (disease management use case), the user is a case manager looking to identify diabetic patients for case management. In such a situation the presented data may include a table with basic patient information and a column indicating whether a patient is diabetic or not based upon patient true state findings. Since the case manager benefits from identifying all diabetic patients, the evidentiary threshold used to determine who a diabetic is may be relatively low (true state determinations with a lower confidence threshold). In contrast, a cardiologist may be interested in a different pathology, such as acute heart failure, and may desire to have more pinpointed results. As such the columns would reflect this other pathology, and the evidentiary standards may be higher (only true state data with very high confidence values). In turn, this could be contrasted with a coder looking for patients with a pathology for MediCare submission, which has yet another evidentiary standard (evidence in a single source document, "green zone" finding, etc.).

After the structured data set has been generated for presentation, the values within the dataset may be enhanced with a link back to the source documentation (at 1320). Since the structured data set is an abstraction of source documentation, enabling a user to efficiently and rapidly reference the evidence is desirable. This link enables a user to reference the source evidence using a single click of a mouse button if they so desire (at 1330).

If the link is selected, the source document is directly accessed and presented with the evidence highlighted and/or otherwise identified (at 1340). If annotations were included when the source document was previously accessed, these annotations can likewise be presented to the user (at 1350). The user than has the option to update the annotations, factual conclusion, etc. (at 1360). For example, a user could identify that the evidence is not properly attributed to the correct pathology, and the annotation and finding can be updated accordingly.

If the annotation and/or finding have been updated by the user, the data warehouse may be updated to reflect these new values and evidence links (at 1370). Thus, the structured data presented to the user will now reflect the correct findings and evidence.

Annotation of data presented by in the data warehouse can be used for a number of applications. For example, in the disease management use case described above, classification of patients by the urgency, acuteness and medical priority of their conditions and recent clinical events (current, reliable data vs stale or inaccurate) may be annotated by a coder or case manager to reflect a difference case management priority or interpretation of the data.

Another application of data annotation in this context is identification of data inconsistencies, stale, incorrect or outdated information (e.g. patient is deceased, or condition no longer applies, as in foot ulcer on a patient with below knee amputation).

Further, data warehouse management and extracted data annotation can be applied to identification of inefficient, low value or redundant care activities. These activities may be categorized by value/benefit, ROI classification, or other useful metric.

III. Examples

FIGS. 14-18 provide example screenshots of user views of the system employing annotations and data warehouse management. It should be realized that these screenshots are provided by way of example, and do not restrict the scope of the embodiments.

Figure 14:
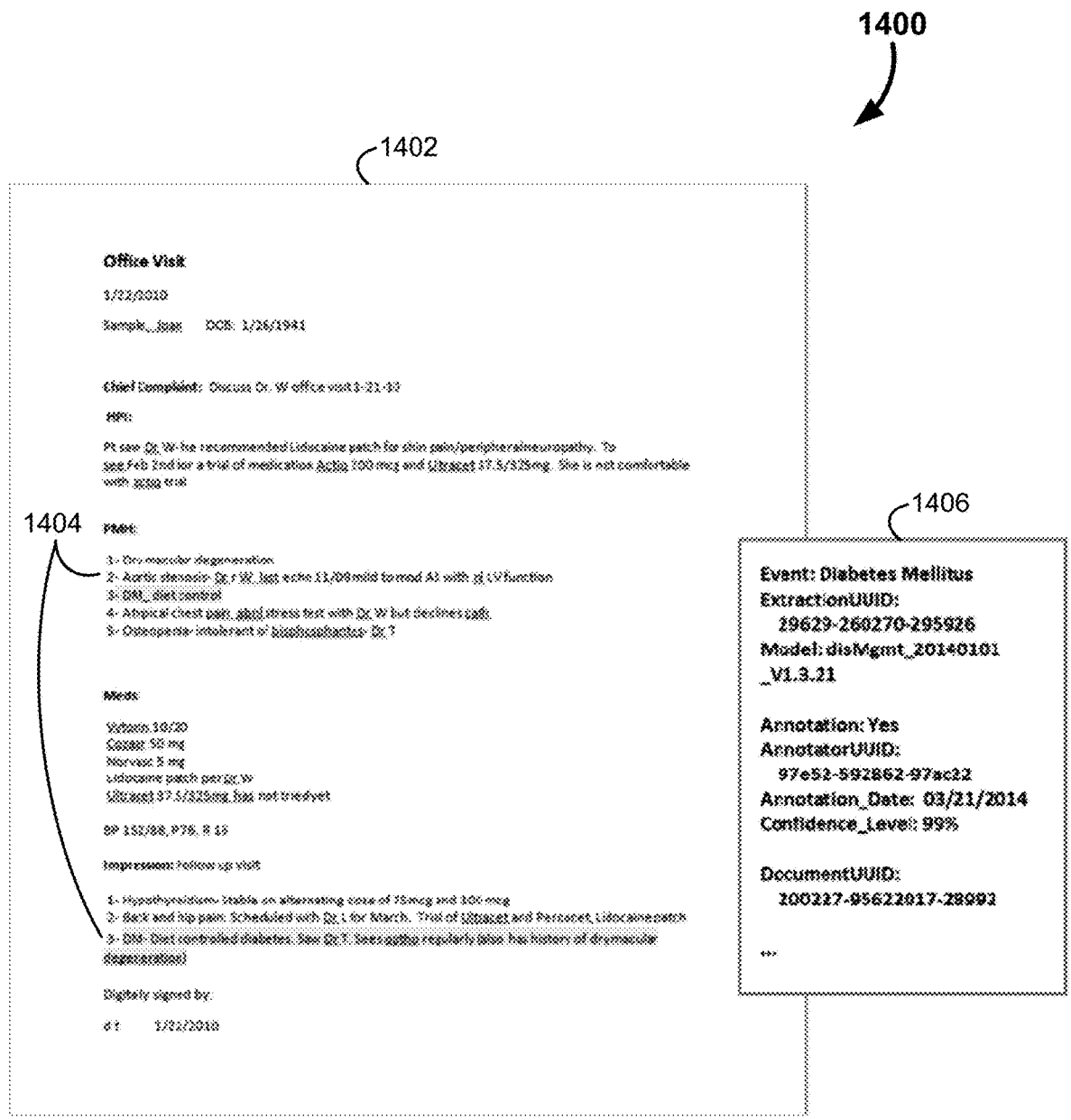

FIG. 14 provides a screen shot of patient information, shown generally at 1400. The patient record source document is provided at 1402. Evidence has been highlighted at 1404. A finding summary box associated with the evidence is also provided at 1406. In some embodiments this summary box may include a true statement regarding the patient that has been generated by the first pass review of the patient's records. Here, the finding summary includes the true state (here diabetes), extraction ID and associated model used in the extraction/inference of the true state. The summary may likewise indicate if the evidence has been annotated, the ID of the annotator, date of annotation, and confidence level for the inferred true state. The source document ID is also provided.

Figure 15:
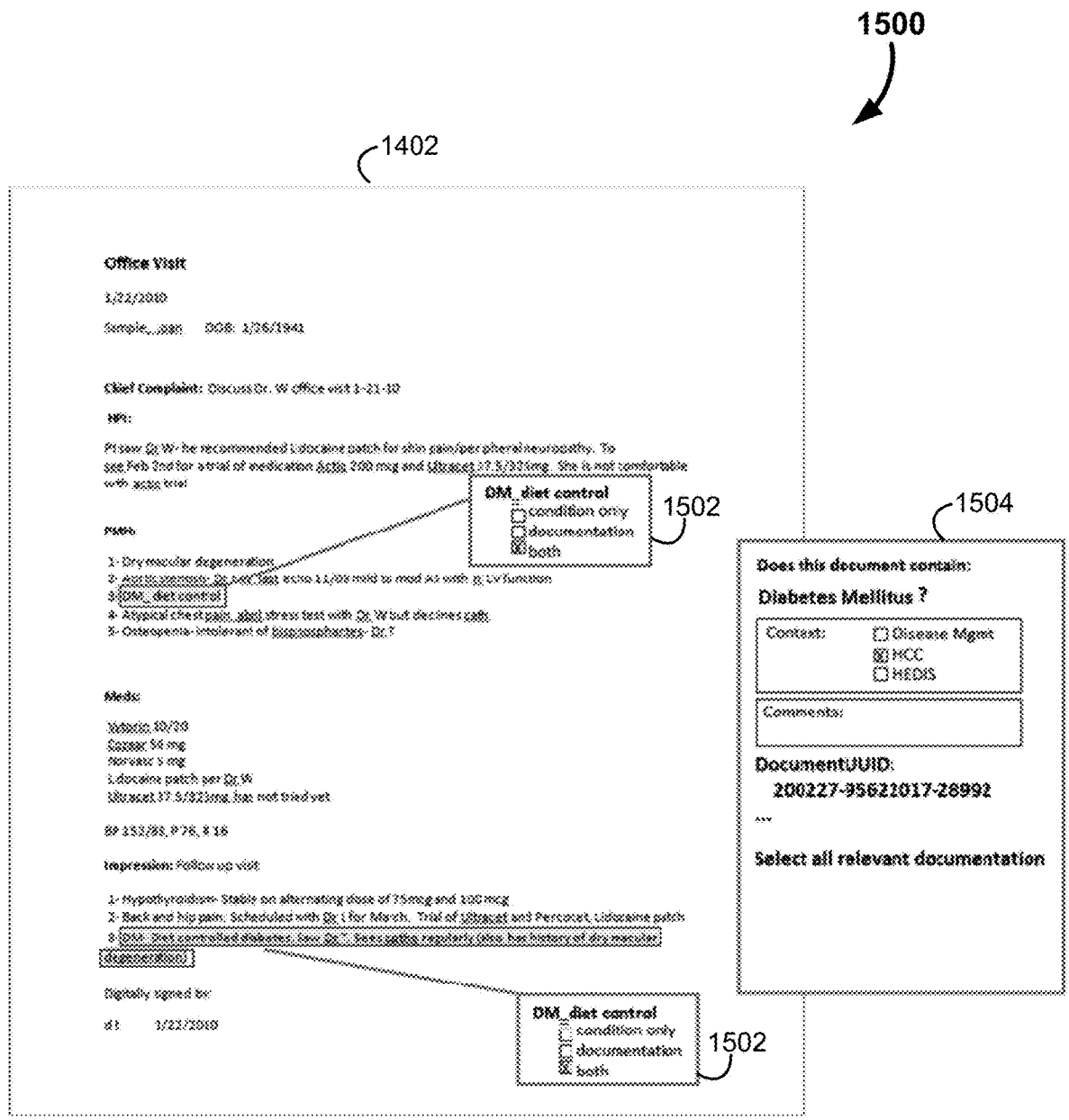

FIG. 15 provides another screenshot where an embodiment of the specific true state validation is being performed, shown generally at 1500. Like wish the previous screenshot, the source document is provided at 1402, and the evidence is provided as highlighted. Here however, the user is being queried for each piece of highlighted evidence whether the evidence is a condition and/or documentation, shown at the call out boxes 1502. Likewise, the user is being queried whether the document contains a finding for diabetes at 1504. The context of the finding, and a customizable annotation, may also be provided at the query box 1504.

Figure 16:
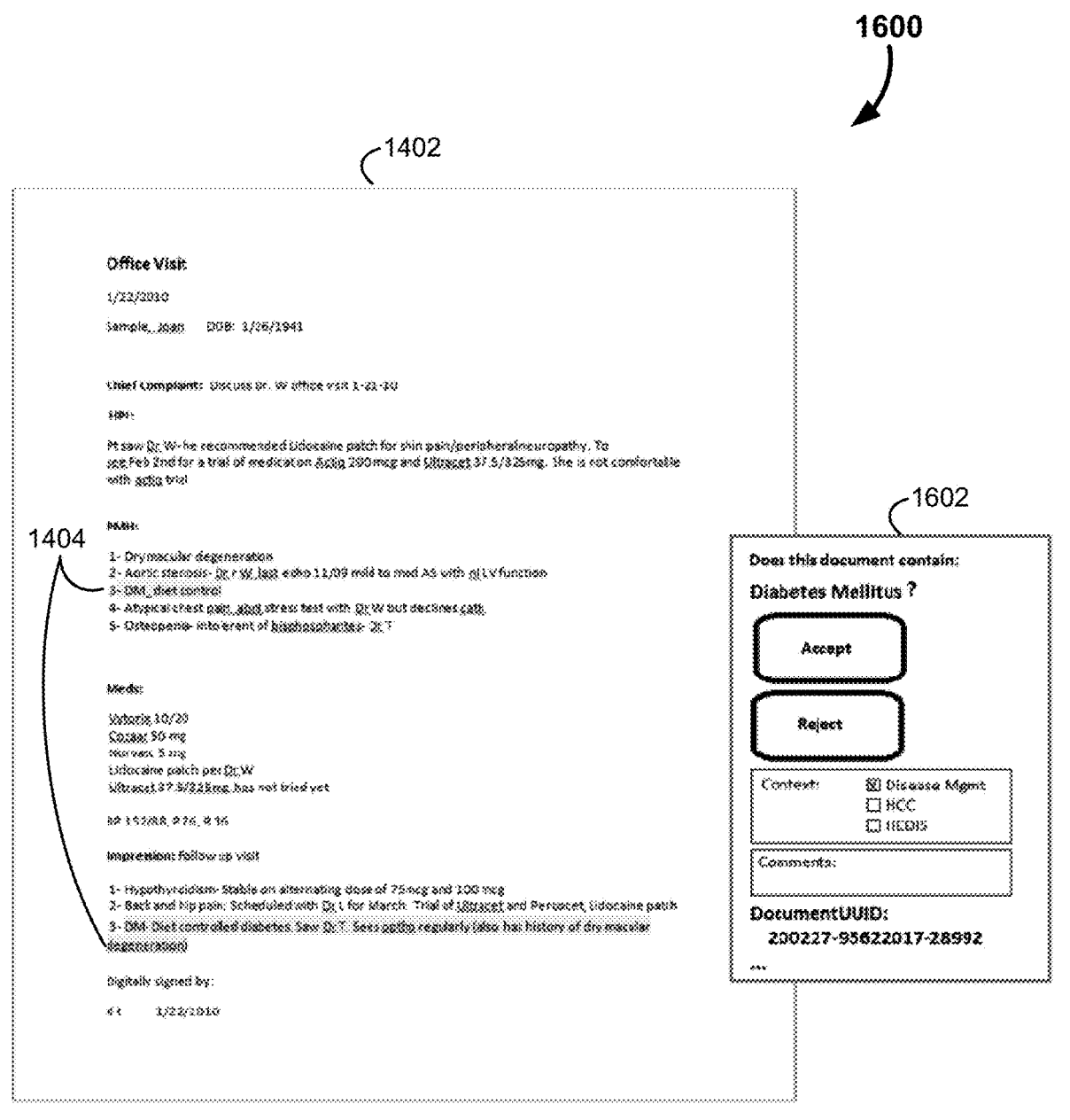

FIG. 16 provides another embodiment for specific finding validation, shown generally at 1600. Again the source document 1402 and the highlighted evidence 1404 are presented to the user. However here, a simple yes/no question is presented to the user at the query box 1602. Context and free-form annotation are also available for the user's input.

Figure 17:
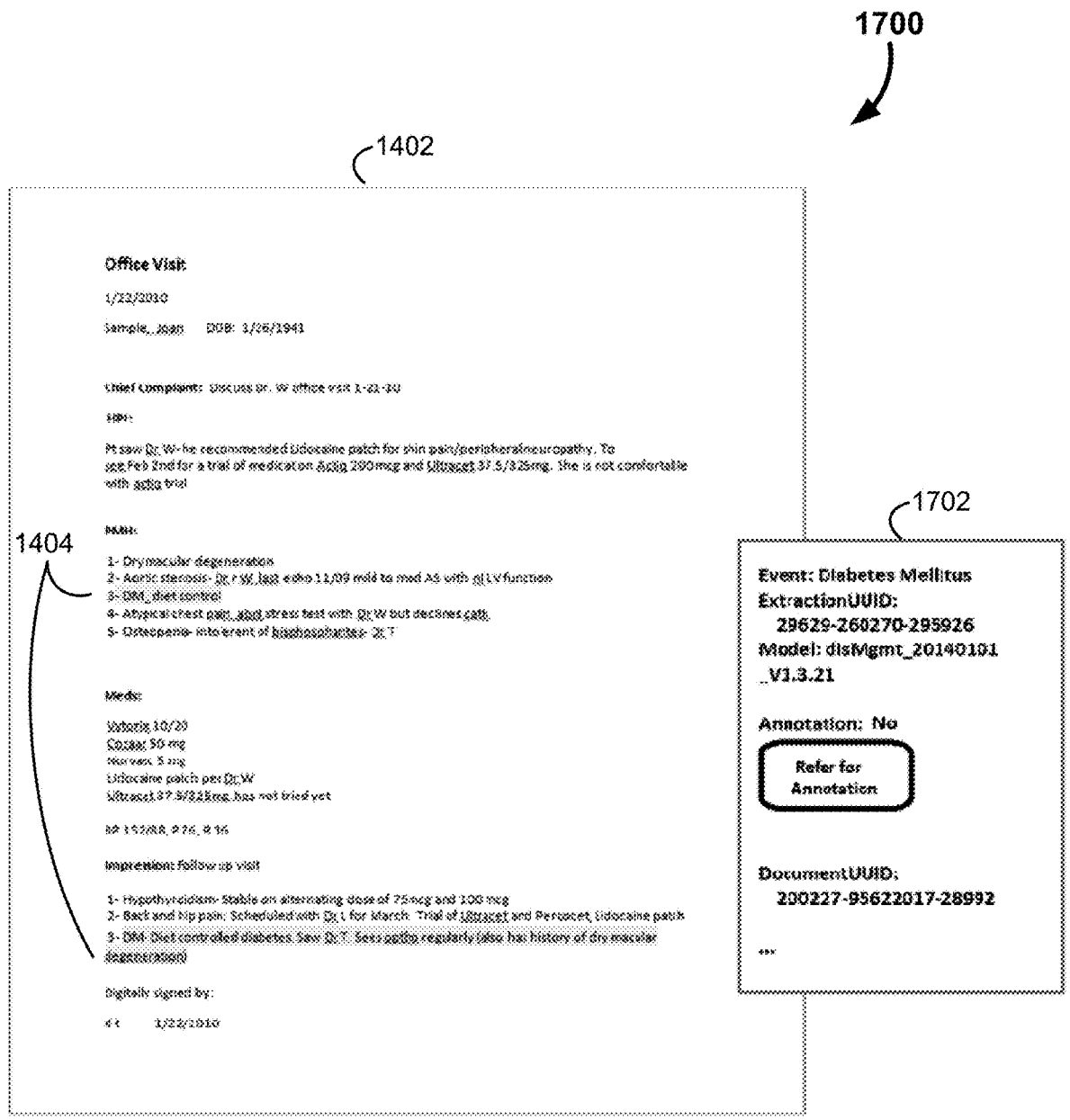

FIG. 17 provides a screenshot where no annotation has been provided, and the user may select to refer out the evidence for annotation, shown generally at 1700. Again, the evidence 1404 is shown highlighted in the source document 1402. The summary box 1702 includes the finding, extraction ID and model. However, here it is indicated that no annotation is available, and the user has a button that allows them to refer the evidence out for annotation.

FIG. 18 provides a registry report for the data warehouse, shown generally at 1800. This report is a tabular structured format that has been extracted from the source documents using natural language processing and/or predictive models to perform a probabilistic transformation of the unstructured source data into this registry. In this example, patient name, basic physiological data (blood pressure, dates, cholesterol, A1c, smoking status, etc.) are listed. Additionally, a condition diagnosis (true state) is provided in the table as a simple "yes/no" selection. These diagnoses have been generated using the evidence in the source document(s) via the first pass processes previously discussed. These diagnoses are linked, allowing the user to reference the source document, with a single click, from this structured data set. When a link is selected, the source document is presented with the evidence highlighted in a manner similar to what is shown in FIG. 14.

IV. System Embodiments

Figure 19A:
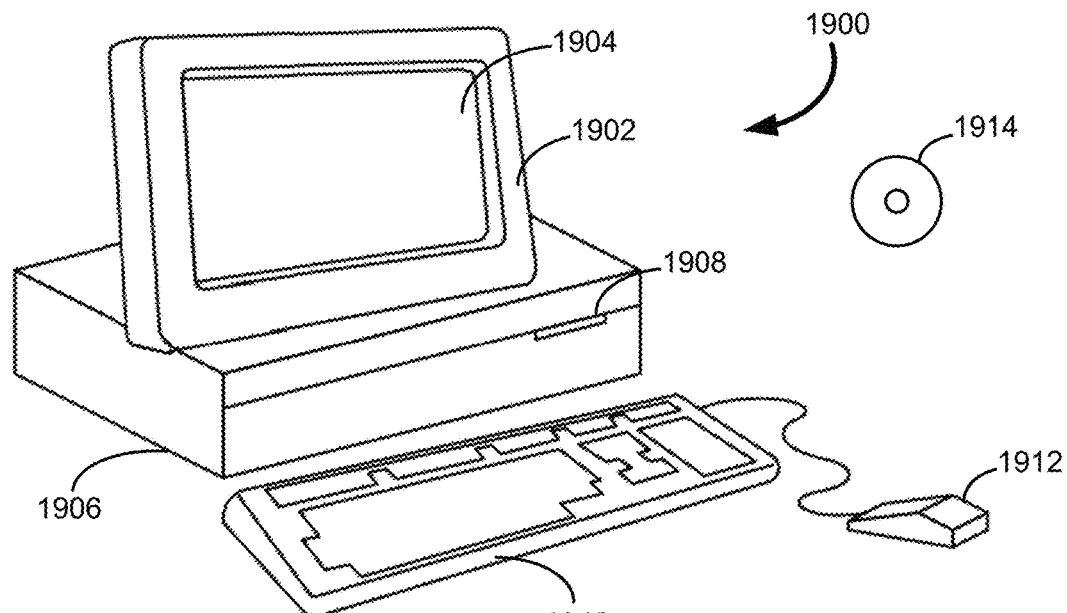
FIGS. 19A and 19B are example illustrations of a computer system capable of embodying the current invention.
Figure 19B:
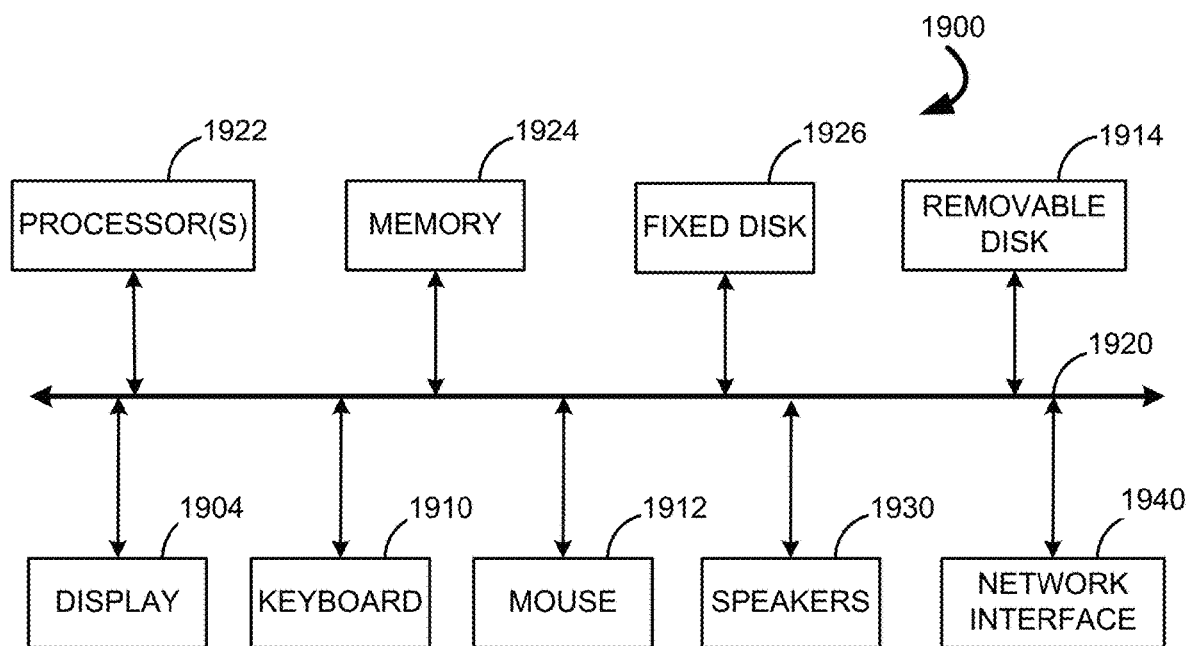

FIGS. 19A and 19B illustrate a Computer System 1900, which is suitable for implementing embodiments of the present invention. FIG. 19A shows one possible physical form of the Computer System 1900. Of course, the Computer System 1900 may have many physical forms ranging from a printed circuit board, an integrated circuit, and a small handheld device up to a huge super computer. Computer system 1900 may include a Monitor 1902, a Display 1904, a Housing 1906, a Disk Drive 1908, a Keyboard 1910, and a Mouse 1912. Disk 1914 is a computer-readable medium used to transfer data to and from Computer System 1900.

FIG. 19B is an example of a block diagram for Computer System 1900. Attached to System Bus 1920 are a wide variety of subsystems. Processor(s) 1922 (also referred to as central processing units, or CPUs) are coupled to storage devices, including Memory 1924. Memory 1924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1926 may also be coupled bi-directionally to the Processor 1922; it provides additional data storage capacity and may also include any of the computer-readable media described below. Fixed Disk 1926 may be used to store programs, data, and the like and is typically a secondary storage medium (such as a hard disk) that is slower than primary storage. It will be appreciated that the information retained within Fixed Disk 1926 may, in appropriate cases, be incorporated in standard fashion as virtual memory in Memory 1924. Removable Disk 1914 may take the form of any of the computer-readable media described below.

Processor 1922 is also coupled to a variety of input/output devices, such as Display 1904, Keyboard 1910, Mouse 1912 and Speakers 1930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1922 optionally may be coupled to another computer or telecommunications network using Network Interface 1940. With such a Network Interface 1940, it is contemplated that the Processor 1922 might receive information from the network, or might output information to the network in the course of performing the above-described first pass analysis of medical records for personalization of care and/or management of MediCare audit risk. Furthermore, method embodiments of the present invention may execute solely upon Processor 1922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

Although the invention has been described in terms of specific embodiments, it is anticipated that alterations and modifications thereof will no doubt become apparent to those skilled in the art. It is therefore intended that the following claims be interpreted as covering all such alterations and modification as fall within the true spirit and scope of the invention.

What is claimed is:

1. In a health information management system, a method for personalizing medical care, the method comprising:
receiving a plurality of medical records for a patient;
identifying terms by cross referencing language nodes in the plurality of medical records against a wiki-like database;

identifying medical concepts through machine learned relational clustering of the terms:

inferring a true state for the patient using a processor by applying a predictive model to the medical concepts, wherein the true state is a condition of the patient;

identifying medical resources for the patient using a state machine based upon the true state, the patient's condition and care already received;

scheduling the medical resources for the patient; and aggregating the true state of a plurality of patients for at least one of estimating actuarial risks for price determination, tracking physician performance, and profiling a provider.

2. The method of claim 1 further comprising generating a confidence level for the inferred true state.

3. The method of claim 1 wherein the medical resources include any of laboratory services, diagnostics, therapies and medications.

4. The method of claim 1 further comprising scheduling lab or diagnostic procedures in advance of an appointment based upon the true state data.

5. The method of claim 1 further comprising filling documentation gaps using the true state.

6. The method of claim 1 further comprising identifying items that require additional documentation using the true state.

7. The method of claim 1 further comprising tracking follow-up.

8. The method of claim 2 further comprising validating the true state.

9. The method of claim 8 wherein the validation updates the predictive model and updates the confidence level for the inferred true state.

10. The method of claim 8 further comprising optimizing routing of evidence for validation based upon greatest impact the evidence has on the true state inference.

11. A health information management system for personalizing medical care comprising:

a records database configured to receive a plurality of medical records for a patient; and a first pass analyzer including a processor configured to:

identify terms by cross referencing language nodes in the plurality of medical records against a wiki-like database;

identify medical concepts through machine learned relational clustering of the terms;

infer a true state for the patient by applying a predictive model to the medical concepts; and identify medical resources for the patient using a state machine based upon the true state, the patient's condition and care already received;

schedule the medical resources for the patient; and aggregate the true state of a plurality of patients for at least one of estimating actuarial risks for price determination, tracking physician performance, and profiling a provider.

12. The system of claim 11 wherein the first pass analyzer is further configured to generate a confidence level for the inferred true state.

13. The system of claim 11 wherein the medical resources include any of laboratory services, diagnostics, therapies and medications.

14. The system of claim 11 wherein the first pass analyzer is further configured to schedule lab or diagnostic procedures in advance of an appointment based upon the true state data.

15. The system of claim 11 wherein the first pass analyzer is further configured to fill documentation gaps using the true state.

16. The system of claim 11 wherein the first pass analyzer is further configured to identify items that require additional documentation using the true state.

17. The system of claim 11 wherein the first pass analyzer is further configured to track follow-up.

18. The system of claim 12 further comprising a validation system configured to validate the true state.

19. The system of claim 18 wherein the validation system updates the predictive model and updates the confidence level for the inferred true state.

20. The system of claim 18 further comprising a routing optimizer configured to optimizing routing of evidence for validation based upon greatest impact the evidence has on the true state inference.

* * * * *